US011141430B1

(12) United States Patent
Koneru et al.

(10) Patent No.: US 11,141,430 B1
(45) Date of Patent: Oct. 12, 2021

(54) PHOSPHATE COMPOSITIONS WITH A LOW ALUMINUM CONTENT

(71) Applicant: Exela Sterile Medicines LLC, Lenoir, NC (US)

(72) Inventors: Phanesh Koneru, Lenoir, NC (US); John Maloney, Lenoir, NC (US); Aruna Koganti, Lenoir, NC (US)

(73) Assignee: EXELA STERILE MEDICINES LLC, Lenoir, NC (US)

( * ) Notice: Subject to any disclaimer, the term of this patent is extended or adjusted under 35 U.S.C. 154(b) by 0 days.

(21) Appl. No.: 17/067,253

(22) Filed: Oct. 9, 2020

(51) Int. Cl.
*A61K 33/42* (2006.01)
*A61K 9/00* (2006.01)
*A61K 9/08* (2006.01)

(52) U.S. Cl.
CPC ............ *A61K 33/42* (2013.01); *A61K 9/0029* (2013.01); *A61K 9/08* (2013.01)

(58) Field of Classification Search
CPC ..... A61K 33/42; A61K 9/0029; A61K 9/0019
See application file for complete search history.

(56) References Cited

U.S. PATENT DOCUMENTS 10,632,150 B1 * 4/2020 Thomas .................. A61K 47/02

OTHER PUBLICATIONS

Poole et al., "Aluminum in Pediatric Parenteral Nutrition Products: Measured Versus Labeled Content," The Journal of Pediatric Pharmacoloty and Therapeutics, 2011, pp. 92-97, vol. 16, No. 2.
Hernandez-Sanchez et. al, "Aluminum in parenteral nutrition: a systemic review," European Journal or Clinical Nutrition, 2013, pp. 230-238, vol. 67.
Potassium Phosphates Injection Prescribing Information, CMP Pharma Inc., Revised Sep. 2019, 9 pages.
Potassium Phosphates Injection Prescribing Information, Fresenisu Kabi, Revised Nov. 2019, 9 pages.
Potassium Phosphates Injection Prescribing Information, Hospira, Inc., Revised Jul. 2017, 3 pages.
Sodium Phosphates Injection Prescribing Information, Fresenius Kabi, Revised Dec. 2019, 8 pages.
Sodium Phosphates Injection Prescribing Information, Hospira, Inc. Revised Feb. 2018, 4 pages.

* cited by examiner

*Primary Examiner* — Bethany P Barham
*Assistant Examiner* — Peter Anthopolos
(74) *Attorney, Agent, or Firm* — Polsinelli PC

(57) ABSTRACT

The present disclosure provides compositions comprising phosphate salts having low levels of aluminum, as well as other elemental impurities. In general, phosphate salts compositions disclosed herein are liquid compositions (e.g., admixtures, solutions) comprising in situ formed phosphate salts, a pharmaceutically acceptable carrier, and less than about 250 μg/L of aluminum. Phosphate salts solutions disclosed herein are stable over time (e.g., the amount of total phosphorus and/or the ratio of phosphate salts and/or the level of aluminum does not substantially vary, and the compositions remain free of visible particulate matter). The compositions do not require storage at less than ambient (room) temperature, i.e., no refrigeration is needed. Also provided herein are methods and systems for preparing in situ phosphate salts compositions, and methods of using phosphate salt compositions to provide phosphorous to individuals in need thereof.

18 Claims, No Drawings

PHOSPHATE COMPOSITIONS WITH A LOW ALUMINUM CONTENT

FIELD OF THE INVENTION

The present disclosure relates to stable phosphate compositions having extremely low aluminum content.

BACKGROUND OF THE INVENTION

Phosphorus in the form of organic and inorganic phosphate has a variety of biochemical functions in all organs and tissues, including critical roles in nucleic acid structure, energy storage and transfer, cell signaling, cell membrane composition and structure, acid-base balance, mineral homeostasis and bone mineralization. Concentrated solutions containing a mixture of monobasic and dibasic phosphate salts in Water for Injection (e.g., Sodium Phosphates Injection, USP and Potassium Phosphates Injection, USP) are administered after dilution by the intravenous route as an electrolyte replenisher. The specified storage conditions for these solutions depend on the manufacturer, in part to mitigate the formation of particulate matter and increases in aluminum content.

Aluminum is a contaminant commonly found in parenteral nutrition additive solutions. Research indicates that patients with impaired kidney function, including neonates, who receive parenteral levels of aluminum at greater than 4 to 5 µg per kg per day accumulate aluminum at levels associated with central nervous system and bone toxicity. In an attempt to limit the risk of aluminum toxicity, the U.S. Food and Drug Administration (FDA) has rules limiting the total aluminum content in intravenous formulations. Since some preparations of phosphates solutions can contain up to 15,000 µg/L of aluminum, the total daily aluminum limit may be exceeded. Thus, preparations of phosphates solutions with reduced levels of aluminum would be beneficial.

SUMMARY OF THE INVENTION

Among the various aspects of the present disclosure is the provision of liquid compositions of phosphate salts, each of which includes a pharmaceutically acceptable carrier (e.g., water), in situ formed phosphate salts typically of the same cation (e.g., a monobasic phosphate salt and a dibasic phosphate salt of calcium, potassium, sodium, etc.), and less than about 250 µg/L of aluminum. In some embodiments, the aluminum content may be substantially lower than 250 µg/L; for instance, the aluminum content of some embodiments may be less than about 100 µg/L, less than about 75 µg/L, less than about 50 µg/L, less than about 25 µg/L, or even less than about 17 µg/L. In some embodiments, the aluminum content may range from about 0 µg/L to about 100 µg/L, about 0 µg/L to about 50 µg/L, or from about 0 µg/L to less than 17 µg/L. The aluminum content of some compositions described herein may be characterized with respect to specific storage conditions. For instance, the aluminum content of some embodiments may be less than about 250 µg/L or less than about 100 µg/L when the solution is stored in a container for 6 months, 12 months, 18 months, or 24 months at 25° C. and 40% relative humidity, or for 6 months, 12 months, 18 months, or 24 months at 40° C. and 25% relative humidity.

The compositions set forth above are typically devoid of visible particulate matter. For instance, a composition may be devoid of visible particulate matter when stored for 6 months, 12 months, 18 months or 24 months at 25° C. and 40% relative humidity or stored for 6 months, 12 months, 18 months, or 24 months at 40° C. and 25% relative humidity. The compositions do not require refrigerated storage conditions to remain stable and maintain their extremely low aluminum content. Put differently, unlike some prior art compositions which require refrigerated storage conditions, the currently presented compositions can be stored throughout their shelf life at room temperature to retain their stability and extremely low aluminum content.

The compositions set forth above may have a specific molar ratio of phosphate salts. For instance, some embodiments may have a molar ratio of a monobasic phosphate salt to a dibasic phosphate salt that is about 1:1 to about 2:1. In certain iterations, a composition comprises about 3 millimoles total phosphorus/mL and about 4 mEq to about 4.5 mEq of Na+ or K+ per milliliter of Water for Injection. In specific embodiments, the in situ formed phosphate salts are in an amount that provides about 3 millimoles total phosphorus/mL and about 4 mEq to about 4.5 mEq of Na+ or K+ per milliliter of Water for Injection.

Some embodiments of the compositions set forth above may be characterized as being sterile and/or formulated for injection (e.g., intravenous injection).

Another aspect of the present disclosure provides a container (e.g., a silica-lined vial or COP vial) having a filter sterilized and/or a terminally sterilized phosphate salts composition (such as any of those described above) disposed therein. The vial may be sealed in any appropriate manner (e.g., with a cap) and may include a pierceable septum or the like to enable the solution to be drawn therefrom for administration (e.g., intravenous administration) to individuals. In certain iterations, the composition in the vial comprises about 3 millimoles total phosphorus/mL and about 4 mEq to about 4.5 mEq of Na+ or K+ per milliliter of Water for Injection. The phosphate salts solution in the container is stable for at least 6, 12, 18, or 24 months when the container is stored at 25° C. and 40% relative humidity.

Yet another aspect of the present disclosure encompasses a total parenteral nutrition formulation or a standard electrolyte formulation for intravenous administration that includes a phosphate salts composition described herein.

Still another aspect of the present disclosure encompasses a liquid composition comprising ortho-phosphoric acid, a cationic base selected from potassium hydroxide and sodium hydroxide, and Water for Injection, wherein the o-phosphoric acid and cationic base are in an amount that provides about 3 millimoles phosphate per mL and about 4 to about 4.5 mEq of cation (e.g., K+ or Na+) per mL, and wherein the composition contains less than about 250 µg/L of aluminum. In some embodiments, the aluminum content may be substantially lower than 250 µg/L; for instance, the aluminum content of some embodiments may be less than about 100 µg/L, less than about 75 µg/L, less than about 50 µg/L, less than about 25 µg/L, or even less than about 17 µg/L. In some embodiments, the aluminum content may range from about 0 µg/L to about 100 µg/L, 0 µg/L to about 50 µg/L, or from about 0 µg/L to less than 17 µg/L.

Still another aspect of the present disclosure encompasses a system comprising (a) a composition comprising or consisting essentially of ortho-phosphoric acid, sodium hydroxide, and Water for Injection, wherein the ortho-phosphoric acid and sodium hydroxide are in stoichiometric amounts that provide about 3 mmol P/mL and about 4.0 to about 4.5 mEq Na+ or K+/mL, respectively, and the composition contains less than about 250 µg/L of aluminum or less than about 100 µg/L of aluminum; (b) a mixing vessel containing the composition of (a); and (c) an apparatus operable to cool the composition in the mixing vessel.

Still another aspect of the present disclosure encompasses a process for preparing a pharmaceutical solution comprising a monobasic sodium phosphate and dibasic sodium phosphate in a molar ratio of about 2 to about 1, respectively, the method comprising (a) mixing an amount of ortho-phosphoric acid that provides about 3 millimoles phosphorus per mL and an amount of sodium hydroxide that provides about 4 mEq of Na+ per mL in Water for Injection to obtain a clear solution, wherein the clear solution has less than about 50 µg/mL of aluminum, and (b) sterilizing the pharmaceutical solution by filter sterilization and/or terminal sterilization. In some embodiments, the aluminum content may be less than 40 µg/L, less than 30 µg/L, less than 20 µg/L, or less than 17 µg/L of aluminum. The solution can be dispensed into an appropriate container (e.g., a vial) after filter sterilization, and maybe further subjected to terminal sterilization.

Still another aspect of the present disclosure encompasses a process for preparing a pharmaceutical solution comprising a monobasic potassium phosphate and dibasic potassium phosphate in a molar ratio of about 1.2 to about 1, respectively, the method comprising (a) mixing (e.g., stirring, agitating, or the like) an amount of ortho-phosphoric acid that provides about 3 millimoles phosphorus per mL and an amount of potassium hydroxide that provides about 4.4 mEq of K+ per mL in Water for Injection to obtain a clear solution, wherein the clear solution has less than 100 µg/L of aluminum, and (b) sterilizing the pharmaceutical solution by filter sterilization and/or terminal sterilization. In some embodiments, the aluminum content may be less than 75 µg/L, less than 50 µg/L, or less than 20 µg/L. The solution can be dispensed into an appropriate container (e.g., a vial, a bag) after filter sterilization and may be further subjected to terminal sterilization.

In some embodiments of the above-described processes, the temperature of the mixture may be controlled. For example, the temperature may not exceed 80° C., or 70° C., or 60° C. In some instances, the temperature may be about 55° C. or less, about 50° C. or less, about 45° C. or less, or about 45° C. or less.

In specific iterations of the process, stoichiometric amounts of phosphoric acid and sodium/potassium hydroxide are used such that additional buffers, acids, or bases are not needed to adjust or control the pH of the final solution.

Other aspects and iterations of the invention are described more thoroughly below.

DETAILED DESCRIPTION

Attempts by the applicant to improve the quality of existing drug products comprising phosphate salts (e.g., Sodium Phosphates Injection, USP; Potassium Phosphates Injection, USP) initially focused on the drug substances, namely monobasic and dibasic phosphate salts. Drug substances were obtained from multiple vendors and assayed for impurities. Lot-to-lot variability of aluminum, both from a single vendor and among vendors, was higher than desired. The variability and high aluminum content is likely due to the fact that phosphate salts are mined from a quarry, rather than synthesized in a manufacturing plant. Because aluminum is the earth's third most abundant mineral, the phosphate salts are contaminated with aluminum in significant amounts. Based on the high risk of the aluminum content, a reliable source for the drug substances could not be secured. Further purification of the drug substances, or the finished drug product, to reduce aluminum was considered but not pursued due to high costs. In situ generation of the drug substances was ultimately pursued as a means to obtain a finished drug product with reproducibly low aluminum content.

Accordingly, the present disclosure provides compositions comprising phosphate salts having low levels of aluminum, as well as other elemental impurities. In general, phosphate salts compositions disclosed herein are liquid compositions (e.g., admixtures, solutions) comprising in situ formed phosphate salts, a pharmaceutically acceptable carrier, and less than about 250 µg/L of aluminum. In some instances, phosphate salts compositions disclosed herein contain less than about 100 µg/L of aluminum. In other instances, phosphate salts compositions disclosed herein contain less than about 50 µg/L of aluminum, less than about 25 µg/L of aluminum, or even less than about 17 µg/L of aluminum. Phosphate salts solutions described herein may be used as a source of phosphate, for addition to large volume intravenous fluids, to prevent or correct hypophosphatemia, or for use as an additive in total parenteral fluid formulas. Advantageously, phosphate salts solutions disclosed herein are stable over time (e.g., the amount of total phosphorus and/or the ratio of phosphate salts and/or the level of aluminum does not substantially vary, and the compositions remain free of visible particulate matter). Also provided herein are methods and systems for preparing in situ phosphate salts compositions, and methods of using phosphate salt compositions to provide phosphorous to individuals in need thereof.

I. Definitions

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

When introducing elements of the embodiments described herein, the articles "a", "an", "the" and "said" are intended to mean that there are one or more of the elements. The terms "comprising", "containing", "including" and "having" are intended to be inclusive and mean that there may be additional elements other than the listed elements.

The term "about," generally is meant to encompass deviations of plus or minus five percent, as modified by the context in which the term is used.

The term "stable composition" means a composition has an amount or level of a critical attribute that does not substantially change over time, and the composition remains free of visible particulate matter. In some aspects, "stable composition" refers to pharmaceutical compositions that comply with ICH guidelines as generally followed in the pharmaceutical arts.

The term "USP" refers to "The United States Pharmacopeia."

The term "Water for Injection" refers to non-pyrogenic water suitable for intravenous administration. The Water for Injection may be as per USP specifications.

II. Compositions

The present disclosure encompasses several different types of compositions. One aspect of the present disclosure provides compositions comprising phosphate salts, wherein some or all the phosphate salts are formed in situ. The term "phosphate salt formed in situ" and the term "in situ formed phosphate salt" are interchangeable, and refer to a phosphate salt that is formed during manufacturing of the composition from starting materials of the manufacturing process (i.e., ortho-phosphoric acid and a cationic base). In another aspect, the present disclosure provides compositions comprising ortho-phosphoric acid, a cationic base, and a pharmaceutically acceptable carrier. Features of compositions comprising ortho-phosphoric acid, a cationic base, and a pharmaceutically acceptable carrier are also described in Section III (e.g., suitable sources of o-phosphoric acid and a cationic base, preferred temperatures, etc.).

In situ formed phosphate salts are never isolated or purified during the manufacturing process. Preferably, at least 50% of the phosphate salts in a composition of the present disclosure are phosphate salts formed in situ. In various embodiments, at least 70%, at least 80%, at least 90%, at least 95%, or at least 99% of the phosphate salts in a composition of the present disclosure are phosphate salts formed in situ. In a specific embodiment, the present disclosure provides compositions comprising phosphate salts, wherein all of phosphate salts are in situ formed phosphate salts—stated another away, the manufacturing process of said composition does not involve any amount of a phosphate salt as a starting material. Thus, in another specific embodiment, the present disclosure provides compositions consisting essentially of ortho-phosphoric acid, a cationic base, and a pharmaceutically acceptable carrier.

Typically, phosphate salts compositions disclosed herein contain phosphate salts of a single cation (e.g., calcium, or potassium, or sodium, etc.) and phosphate. For instance, phosphate salts of sodium and phosphate may be monobasic sodium phosphate ($NaH_2PO_4$), dibasic sodium phosphate ($Na_2HPO_4$), and trisodium phosphate ($Na_3PO_4$). As another example, phosphate salts of potassium and phosphate may be monobasic potassium phosphate ($KH_2PO_4$), dibasic sodium potassium ($K_2HPO_4$), and tripotassium phosphate ($K_3PO_4$). Thus, a composition comprising phosphate salts of sodium and phosphate is understood to comprise two or more sodium phosphate salts (e.g., monobasic sodium phosphate, dibasic sodium phosphate, trisodium phosphate). Similarly, compositions disclosed herein comprising ortho-phosphoric acid, a cationic base, and a pharmaceutically acceptable carrier also typically contain a cationic base of a single cation (e.g., calcium, or potassium, or sodium, etc.).

The compositions disclosed herein are generally liquid compositions. For instance, the phosphate salts compositions disclosed herein may be solutions comprising phosphate salts (preferably of a single cation) and a pharmaceutically acceptable carrier. The compositions comprising ortho-phosphoric acid, a cationic base, and a pharmaceutically acceptable carrier are also generally liquid compositions, though the compositions may or may not be characterized as solutions. Suitable pharmaceutically acceptable carriers include but are not limited to Water for Injection, saline, dextrose solutions, and the like, which are of sufficient purity to be included in pharmaceutical formulations. Phosphate salt compositions comprising phosphate salts and a pharmaceutically acceptable carrier may further include a pH adjuster (e.g. a cationic base). Preferably, the cation of the cationic base is the same as the cation of the phosphate salt (e.g., sodium hydroxide for sodium phosphate salts, potassium hydroxide for potassium phosphate salts, etc.). In some embodiments, the phosphate salt composition consists essentially of phosphate salts and a pharmaceutically acceptable carrier. Compositions of the present disclosure preferably do not contain any bacteriostat, antimicrobial agent, or added buffer. Notwithstanding, in some embodiments, phosphate salt solutions of the present disclosure are sterile. Filter sterilization and/or terminal sterilization can be used to produce sterile phosphate salts solutions of the present disclosure. In a specific embodiment, the present disclosure provides a solution comprising or consisting essentially of in situ formed phosphate salts, preferably of a single cation, and Water for Injection, optionally wherein the solution is sterile.

In general, compositions or solutions of the present disclosure contain less than about 250 µg/L of aluminum, for example 250 µg/L, 225 µg/L, 200 µg/L, 175 µg/L, 150 µg/L, 125 µg/L, 100 µg/L, etc. of aluminum. In specific embodiments, the phosphate salts composition or solution may contain less than about 100 µg/L of aluminum, less than about 75 µg/L, or less than about 50 µg/L of aluminum. In some embodiments, the aluminum content may be less than about 95 µg/L, less than about 90 µg/L, less than about 85 µg/L, less than about 75 µg/L, less than about 70 µg/L, less than about 65 µg/L, less than about 60 µg/L, or less than about 55 µg/L. In some embodiments, the aluminum content may be less than about 50 µg/L, less than about 45 µg/L, less than about 40 µg/L, less than about 35 µg/L, less than about 30 µg/L, less than about 25 µg/L, less than about 20 µg/L, or less than about 15 µg/L. In some embodiments, the aluminum content may be less than about 17 µg/L, less than about 10 µg/L, or less than about 5 µg/L. In still other embodiments, the aluminum content may range from about 0 µg/L to about 250 µg/L, about 0 µg/L to about 200 µg/L, about 0 µg/L to about 150 µg/L, about 0 µg/L to about 100 µg/L, from about 0 µg/L to about 90 µg/L, from about 0 µg/L to about 75 µg/L, from about 0 µg/L to about 50 µg/L, from about 0 µg/L to about 20 µg/L, from about 0 µg/L to about 17 µg/L, or from about 0 µg/L to about 10 µg/L. The amount of aluminum in compositions of the present disclosure is determined by inductively coupled plasma mass spectrometry (ICP-MS), unless specifically stated otherwise. Methods for measuring aluminum by inductively coupled plasma spectrometry are known in the art. See, for example, USP <1730>.

Measurement of the aluminum content in the above embodiments may occur during manufacturing (e.g., for a batch solution), at the time of packaging, or after storage in a sealed container under specified conditions (e.g., temperature, relative humidity). Measurement of a composition "at the time of packaging" refers to measurement of a sample obtained from a sealed container comprising the composition on the day the composition was packaged into the container. In a specific embodiment, the present disclosure provides a composition comprising or consisting essentially of o-phosphoric acid, a cationic base selected from potassium hydroxide and sodium hydroxide, and a pharmaceutically acceptable carrier, wherein the composition contains less than about 250 µg/L of aluminum, less than about 200 µg/L of aluminum, less than about 150 µg/L of aluminum, less than about 100 µg/L of aluminum, less than about 75 µg/L of aluminum, or less than about 50 µg/L of aluminum. In another specific embodiment, the present disclosure provides a composition or solution comprising or consisting essentially of in situ formed phosphate salts and a pharmaceutically acceptable carrier, wherein the composition or solution contains less than about 250 µg/L of aluminum, less than about 200 µg/L of aluminum, or less than about 150 µg/L of aluminum at the time of packaging or after storage at 25° C. and 40% relative humidity (RH) for at least 6 months (e.g., at least 6, 9, 12, 13, 14, 15, 16, 17, 18, 19, 20, 21, 22, 23 or 24 months). Typically, the composition or solution is sterile (e.g., filter sterilized and/or terminally sterilized). In another specific embodiment, the present disclosure provides a composition or solution comprising or consisting essentially of in situ formed phosphate salts and a pharmaceutically acceptable carrier, wherein the aluminum content of the composition or solution is less than about 100 µg/L of aluminum, less than about 75 µg/L of aluminum, or less than about 50 µg/L of aluminum at the time of packaging or after storage at 25° C. and 40% relative humidity (RH) for at least 6 months (e.g., at least 6, 9, 12, 13, 14, 15, 16, 17, 18, 19, 20, 21, 22, 23 or 24 months). Typically, the composition or solution is sterile (e.g., filter sterilized and/or terminal sterilized). In another specific embodiment, the present disclosure provides a composition or solution comprising or consisting essentially of in situ formed phosphate salts and a pharmaceutically acceptable carrier, wherein the aluminum content of the composition or solution is less than 17 µg/L of aluminum at the time of packaging or after storage at 25° C. and 40% relative humidity (RH) for at least 6 months (e.g., at least 6, 9, 12, 13, 14, 15, 16, 17, 18, 19, 20, 21, 22, 23 or 24 months). Typically, the composition or solution is sterile (e.g., filter sterilized and/or terminal sterilized).

In general, the phosphate salts compositions and solutions are devoid of visible particulate matter. "Devoid of visible particulate matter" means the solution is essentially free from particles that can be observed on visual inspection. Examples of such particulate matter include, but are not limited to, fibers, glass, metal, elastomeric materials, and precipitates. Precipitates may include precipitated particles or crystals, or crystalline-like visible particles or crystals. Inspection for visible particulate matter may be carried out according to USP <790>. Briefly, a composition or solution is examined without magnification (except for optical correction as may be required to establish normal vision) against a black background and against a white background maintaining illumination at the inspection point of a sufficient minimum intensity (e.g., 2000 and 3750 lux).

In certain embodiments, the phosphate salts composition or solution also has minimal sub-visible particles, as determined by USP <788> Method I. In various embodiments, the phosphate salts composition or solution contains no more than 3000 particulates ≥10 µm and no more than 300 particulates ≥25 µm, or no more than 2500 particulates ≥10 µm and no more than 250 particulates ≥25 µm. In some embodiments, the number of particulates ≥10 µm is no more than 1000, no more than 900, no more than 800, no more than 700, or no more than 600. In still further embodiments, the number of particulates ≥10 µm is no more than 500, no more than 400, no more than 300, or no more than 200. In some embodiments, the number of particulates ≥25 µm is no more than 240, no more than 230, no more than 220, no more than 210, no more than 200, no more than 190, no more than 180, or no more than 170. In further embodiments, the number of particulates ≥25 µm is no more than 160, no more than 150, no more than 140, no more than 130, no more than 120, no more than 110, no more than 100, no more than 90, no more than 80, no more than 70, or no more than 60. In a specific embodiment, the phosphate salts composition or solution contains no more than 2000 particulates ≥10 µm and no more than 200 particulates ≥25 µm.

In another specific embodiment, the phosphate salts composition or solution contains no more than 1000 particulates ≥10 µm and no more than 200 particulates ≥25 µm. In another specific embodiment, the phosphate salts composition or solution contains no more than 750 particulates ≥10 µm and no more than 200 particulates ≥25 µm. In another specific embodiment, the phosphate salts composition or solution contains no more than 600 particulates ≥10 µm and no more than 200 particulates ≥25 µm. In another specific embodiment, the phosphate salts composition or solution contains no more than 300 particulates ≥10 µm and no more than 200 particulates ≥25 µm. In another specific embodiment, the phosphate salts composition or solution contains no more than 300 particulates ≥10 µm and no more than 100 particulates ≥25 µm. In accordance with USP <788> Method I, particulate count is reported per container. For pharmaceutical compositions, the container is typically the final primary packaging for the dosage form (e.g., vial, bag).

As discussed, above, phosphate salts compositions or solutions disclosed herein comprise two or more phosphate salts typically with the same cation. The molar ratio of these phosphate salts may vary in the phosphate salts compositions or solutions of the present disclosure. In some embodiments, the phosphate salt composition or solution comprises two phosphate salts, and the molar ratio of the phosphate salts is about 5:1 to about 1:5. In further embodiments, the molar ratio of the phosphate salts is about 1:3 to about 3:1, about 1:2 to about 2:1, or about 1:1 to about 2:1. In certain embodiments, the phosphate salt composition or solution comprises a monobasic phosphate salt and a dibasic phosphate salt, with the same cation, in a molar ratio of about 1.2:1. For instance, in one example, the phosphate salts composition is a solution comprising or consisting essentially of a pharmaceutically acceptable carrier and in situ formed monobasic potassium phosphate and dibasic potassium phosphate in a molar ratio of about 1.2 to about 1, respectively. In preferred embodiments, the potassium phosphates solution contains less than 200 µg/L of aluminum, less than 150 µg/L of aluminum, less than 100 µg/L of aluminum, less than 75 µg/L of aluminum, less than 50 µg/L of aluminum, less than 25 µg/L of aluminum, less than 20 µg/L of aluminum, less than about 15 µg/L of aluminum, or even less than about 10 µg/L of aluminum. In certain embodiments, the phosphate salt composition or solution comprises a monobasic phosphate salt and a dibasic phosphate salt, with the same cation, in a molar ratio of about 2:1. For instance, in one example, the phosphate salts composition is a solution comprising or consisting essentially of a pharmaceutically acceptable carrier and in situ formed sodium phosphate monobasic and sodium phosphate dibasic in a molar ratio of about 2 to about 1, respectively. In preferred embodiments, the solution contains less than less than 100 µg/L of aluminum, less than 75 µg/L of aluminum, less than 50 µg/L of aluminum, or even less than 40 µg/L of aluminum (e.g., 20 µg/L or less, 19 µg/L or less, 18 µg/L or less, 17 µg/L or less, 16 µg/L or less, etc.).

The total phosphorus concentration in a composition or solution of the present disclosure may vary. For example, the total phosphorus concentration may range from about 1 millimole phosphorus per milliliter (1 mM P/mL) to about 30 mM P/mL. In various embodiments, the total phosphorus concentration may be about 1 mM P/mL to about 10 mM P/mL, about 1 mM P/mL to about 6 mM P/mL, or about 1 mM P/mL to about 3 mM P/mL. In certain embodiments, the total phosphorus concentration may be about 1 mM P/mL, about 2 mM P/mL, about 3 mM P/mL, about 4 mM P/mL, about 5 mM P/mL, about 6 mM P/mL, about 7 mM P/mL, about 8 mM P/mL, about 9 mM P/mL, about 10 mM P/mL, or more. In some specific embodiments, a composition comprising or consisting essentially of o-phosphoric acid, a cationic base, and a pharmaceutically acceptable carrier has a total phosphorous concentration of about 3 mM P/mL (1 mM P=1 mM $PO_4$). In other specific embodiments, a phosphate salts composition or solution comprises or consists essentially of sodium phosphates or potassium phosphates in Water for Injection, and the total phosphorus concentration in the composition or solution is about 3 mM P/mL.

Total phosphorus concentration for a given phosphate salts composition or solution can be calculated by first determining the amount of each salt species (e.g., monobasic, dibasic) and then summing the phosphorus values determined for each salt species. The amount of each salt species (e.g., monobasic, dibasic) is determined in accordance with USP monographs. If the composition comprises additional sources of phosphorus, the amount of those additional sources is also included in the total phosphorus concentration.

The amount of cation in a composition or solution of the present disclosure, expressed as milliequivalent per milliliter (mEq/mL), may also vary. For example, the amount of cation (e.g., $Ca^{2+}$, $Na^+$, $K^+$, etc.) may range from about 1 mEq/mL to about 10 mEq/mL. In various embodiments, the amount of cation in a composition or solution of the present disclosure may be about 1 mEq/mL, about 2 mEq/mL, about 3 mEq/mL, about 4 mEq/mL, about 5 mEq/mL, about 6 mEq/mL, about 7 mEq/mL, about 8 mEq/mL, about 9 mEq/mL, about 10 mEq/mL. In some embodiments, compositions or solutions of the present disclosure comprise sodium phosphates or potassium phosphates and the amount of cation (e.g., $Na^+$ or $K^+$, respectively) in the composition or solution is about 4 mEq/mL to about 5 mEq/mL. In specific embodiments, a phosphate salts composition or solution comprises sodium phosphates in an amount that provides about 4 mEq $Na^+$/mL. For instance, in one example, the phosphate salts composition is a solution comprising or consisting essentially of a pharmaceutically acceptable carrier and in situ formed sodium phosphate salts, wherein the sodium phosphate salts are in an amount that provides about 3 millimoles/mL total phosphorus and about 4 mEq $Na^+$/mL. In preferred embodiments, the sodium phosphates solution contains less than 100 μg/L of aluminum, less than 50 μg/L of aluminum, or even less than 40 μg/L of aluminum (e.g., 20 μg/L or less, 19 μg/L or less, 18 μg/L or less, 17 μg/L or less, 16 μg/L or less, etc.). In still further embodiments, the phosphate salts composition or solution comprises potassium phosphates and each mL contains about 4.4 mEq $K^+$/mL. For instance, in one example, the phosphate salts composition is a solution comprising or consisting essentially of a pharmaceutically acceptable carrier and in situ formed potassium phosphate salts, wherein the potassium phosphate salts are in an amount that provides about 3 millimoles/mL total phosphorus and about 4.4 mEq K+/mL. In preferred embodiments, the solution contains less than 200 μg/L of aluminum, less than 150 μg/L of aluminum, less than 100 μg/L of aluminum, less than 75 μg/L of aluminum, less than about 50 μg/L of aluminum, or even less than about 10 μg/L of aluminum.

The osmolar concentration of the phosphate salts solution may vary depending on the salts in solution. In embodiments comprising phosphate salts in an amount that provides about 3 millimoles/mL total phosphorus and about 4.0 to about 4.5 mEq of a cation (e.g., Na+, K+, etc.), the osmolar concentration may be about 7 to about 8 mOsmol/mL (calculated).

In specific embodiments, the osmolar concentration may be about 7.0 mOsmol/mL (calculated) to about 7.5 mOsmol/mL (calculated).

The pH of the phosphate salts composition or solution may range from about 2.0 to about 9.0. In various embodiments, the pH of the phosphate salts composition or solution may range from about 2.0 to about 4.0, from about 3.0 to about 5.0, from about 4.0 to about 6.0, from about 5.0 to about 7.0, from about 6.0 to about 8.0, or from about 7.0 to about 9.0. In some embodiments, the pH of the phosphate salts composition or solution may be about 5.0 to about 8.0. In other embodiments, the pH of the phosphate salts composition or solution may be about 5.5 to about 7.5. In further embodiments, the pH of the phosphate salts composition or solution may be about 5.0 to about 6.0, or about 5.4 to about 5.6. In other embodiments, the pH of the phosphate salts composition or solution may be about 6.0 to about 7.0, or about 6.2 to about 6.8.

In some exemplary embodiments, the present disclosure provides a liquid composition comprising or consisting essentially of o-phosphoric acid, a cationic base selected from potassium hydroxide and sodium hydroxide, and Water for Injection, wherein the o-phosphoric acid and cationic base provide about 3 millimoles phosphate per mL and about 4 to about 4.5 mEq of cation (e.g., K+ or Na+) per mL, and wherein the composition contains less than about 250 μg/L of aluminum. In specific examples, the composition may contain less than 200 μg/L of aluminum, less than 150 μg/L of aluminum, less than 100 μg/L of aluminum, less than about 75 μg/L of aluminum, less than about 50 μg/L of aluminum, less than about 25 μg/L of aluminum, or less than about 20 μg/L of aluminum. In some embodiments, the composition contains less than 100 μg/L of aluminum, less than 50 μg/L of aluminum, or even less than 40 μg/L of aluminum (e.g., 20 μg/L or less, 19 μg/L or less, 18 μg/L or less, 17 μg/L or less, 16 μg/L or less, etc.). Suitable forms of o-phosphoric acid and sodium hydroxide are described in Section III. The composition may have a volume that is at least about 50 L (e.g., about 50 L, about 100 L, about 150 L, or more). The temperature of the solution is less than about 80° C., or less than about 70° C., or less than about 60° C., preferably about 55° C. or less. In some examples the temperature may be about 50° C. or less, about 45° C. or less, about 40° C. or less, about 35° C. or less, about 30° C. or less, about 25° C. or less, about 20° C. or less. In further examples, the temperature may be about 15° C. to about 60° C., or about 15° C. to about 50° C.

In some exemplary embodiments, the present disclosure provides a solution for parenteral administration comprising in situ formed phosphate salts in a pharmaceutically acceptable carrier, wherein the solution has less than about 250 μg/L of aluminum, or more preferably less than about 100 μg/L of aluminum. The solution may be used as a source of phosphate, for addition to large volume intravenous fluids, to prevent or correct hypophosphatemia, or for use as an additive in total parenteral fluid formulas. In certain embodiments, the pharmaceutically acceptable carrier is Water for Injection and the in situ formed phosphate salts are monobasic and dibasic phosphate salts of potassium or sodium, wherein the phosphate salts are in an amount that provides about 3 millimoles total phosphorus per mL of solution. In further embodiments, the solution has a pH of about 5 to about 7. The solution is preferably free of visible particulate matter and, in further embodiments, the amount of aluminum and/or phosphate salts is stable over time, optionally even in the absence of refrigeration.

In some exemplary embodiments, the present disclosure provides a solution for parenteral administration comprising phosphate salts of a single cation in a pharmaceutically acceptable carrier, wherein the solution has less than about 250 µg/L of aluminum and has no more than 0.00309 millimoles of aluminum for every mole of phosphorus provided by the phosphate salts. In various embodiments, the phosphates solution contains less than about 200 µg/L of aluminum, less than about 150 µg/L of aluminum, or less than about 100 µg/L of aluminum. The solution may be used as a source of phosphate, for addition to large volume intravenous fluids, to prevent or correct hypophosphatemia, or for use as an additive in total parenteral fluid formulas. In certain embodiments, the pharmaceutically acceptable carrier is Water for Injection and the phosphate salts are monobasic and dibasic phosphate salts of potassium or sodium. In further embodiments, the solution has a pH of about 5 to about 7. The solution is preferably free of visible particulate matter and, in further embodiments, the amount of aluminum and/or phosphate salts is stable over time, optionally even in the absence of refrigeration.

In some exemplary embodiments, the present disclosure provides a solution for parenteral administration comprising phosphate salts of a single cation in a pharmaceutically acceptable carrier, wherein the solution has less than about 250 µg/L of aluminum and has no more than 0.00124 millimoles of aluminum for every mole of phosphorus provided by the phosphate salts. In various embodiments, the phosphates solution may contain less than about 75 µg/L of aluminum, less than about 50 µg/L of aluminum, or even less than about 40 µg/L of aluminum (e.g., about 20 µg/L or less, about 19 µg/L or less, about 18 µg/L or less, about 17 µg/L or less, about 16 µg/L or less, etc.). The solution may be used as a source of phosphate, for addition to large volume intravenous fluids, to prevent or correct hypophosphatemia, or for use as an additive in total parenteral fluid formulas. In certain embodiments, the pharmaceutically acceptable carrier is Water for Injection and the phosphate salts are monobasic and dibasic phosphate salts of potassium or sodium. In further embodiments, the solution has a pH of about 5 to about 7. The solution is preferably free of visible particulate matter and, in further embodiments, the amount of aluminum and/or phosphate salts is stable over time, optionally even in the absence of refrigeration.

In some exemplary embodiments, the phosphate salts composition of the present disclosure is a solution comprising or consisting essentially of Water for Injection and in situ formed sodium phosphate salts, wherein the sodium phosphate salts are sodium phosphate monobasic and sodium phosphate dibasic, and the sodium phosphate salts are in an amount that provides about 3 mM/mL total phosphorus and about 4 mM Eq Na+/mL, and wherein the solution has a pH of 5.4 to 5.6 and contains less than 100 µg/L of aluminum. In preferred embodiments, the sodium phosphates solution contains less than about 75 µg/L of aluminum, less than about 50 µg/L of aluminum, or even less than about 40 µg/L of aluminum (e.g., about 20 µg/L or less, about 19 µg/L or less, about 18 µg/L or less, about 17 µg/L or less, about 16 µg/L or less, etc.). The phosphate salts solution is devoid of visible particulate matter. The phosphate salts solution may be sterile. In some embodiments, the phosphate salts solution has a pH greater than 5.4 to about 5.6. In some embodiments, the phosphate salts solution has a pH of about 5.5 to about 5.6. The phosphate salts solution is diluted prior to use by parenteral administration (e.g., for use as a source of phosphate, for addition to large volume intravenous fluids, to prevent or correct hypophosphatemia, or for use as an additive in total parenteral fluid formulas).

In some exemplary embodiments, the phosphate salts composition of the present disclosure is a solution comprising or consisting essentially of Water for Injection and in situ formed sodium phosphate salts, wherein the sodium phosphate salts are monobasic sodium phosphate and dibasic sodium phosphate in about a 2:1 molar ratio, and the sodium phosphate salts are in an amount that provides about 3 mM/mL total phosphorus and about 4 mM Eq Na+/mL, and wherein the solution contains less than 100 µg/L aluminum. In preferred embodiments, the sodium phosphates solution contains less than about 75 µg/L of aluminum, less than about 50 µg/L of aluminum, or even less than about 40 µg/L of aluminum (e.g., about 20 µg/L or less, about 19 µg/L or less, about 18 µg/L or less, about 17 µg/L or less, about 16 µg/L or less, etc.). The phosphate salts solution is devoid of visible particulate matter. The phosphate salts solution may be sterile. In some embodiments, the phosphate salts solution has a pH greater than 5.4 to about 5.6. In some embodiments, the phosphate salts solution has a pH of about 5.5 to about 5.6. The phosphate salts solution is diluted prior to use by parenteral administration (e.g., for use as a source of phosphate, for addition to large volume intravenous fluids, to prevent or correct hypophosphatemia, or for use as an additive in total parenteral fluid formulas).

In some exemplary embodiments, the phosphate salts composition of the present disclosure is a solution comprising or consisting essentially of Water for Injection, about 240 mg/mL monobasic sodium phosphate, and about 142 mg/mL dibasic sodium phosphate, wherein the monobasic sodium phosphate and the dibasic sodium phosphate are formed in situ, and wherein the solution contains less than 100 µg/L aluminum. In preferred embodiments, the sodium phosphates solution contains less than about 75 µg/L of aluminum, less than about 50 µg/L of aluminum, or even less than about 40 µg/L of aluminum (e.g., about 20 µg/L or less, about 19 µg/L or less, about 18 µg/L or less, about 17 µg/L or less, about 16 µg/L or less, etc.). The phosphate salts solution is devoid of visible particulate matter. The phosphate salts solution may be sterile. In some embodiments, the phosphate salts solution has a pH greater than 5.4 to about 5.6. In some embodiments, the phosphate salts solution has a pH of about 5.5 to about 5.6. The phosphate salts solution is diluted prior to use by parenteral administration (e.g., for use as a source of phosphate, for addition to large volume intravenous fluids, to prevent or correct hypophosphatemia, or for use as an additive in total parenteral fluid formulas).

In some exemplary embodiments, the phosphate salts composition of the present disclosure is a solution comprising or consisting essentially of Water for Injection and in situ formed potassium phosphate salts, wherein the potassium phosphate salts are potassium phosphate monobasic and potassium phosphate dibasic, and the potassium phosphate salts are in an amount that provides about 3 mM/mL total phosphorus and about 4.4 mM Eq K+/mL, and wherein the solution has a pH of about 6.0 to about 7.5 and contains less than about 250 µg/L of aluminum. In some embodiments, the pH is about pH 6.2 to about pH 6.8. In some embodiments, the pH is about pH 6.5 to about pH 6.8. In preferred embodiments, the potassium phosphates solution contains less than about 200 µg/L of aluminum, less than about 150 µg/L of aluminum, or less than about 100 µg/L of aluminum. The phosphate salts solution is devoid of visible particulate matter. The phosphate salts solution may be sterile. The phosphate salts solution is diluted prior to use by parenteral administration (e.g., for use as a source of phosphate, for addition to large volume intravenous fluids, to prevent or correct hypophosphatemia, or for use as an additive in total parenteral fluid formulas).

In some exemplary embodiments, the phosphate salts composition of the present disclosure is a solution comprising or consisting essentially of Water for Injection and in situ formed potassium phosphate salts, wherein the potassium phosphate salts are monobasic potassium phosphate and dibasic potassium phosphate in about a 1.2:1 molar ratio, and the potassium phosphate salts are in an amount that provides about 3 mM/mL total phosphorus and about 4.4 mM Eq K+/mL, and wherein the solution contains less than about 250 µg/L of aluminum. In preferred embodiments, the potassium phosphates solution contains less than about 200 µg/L of aluminum, less than about 150 µg/L of aluminum, or less than about 100 µg/L of aluminum. The phosphate salts solution is devoid of visible particulate matter. The phosphate salts solution may be sterile. The phosphate salts solution is diluted prior to use by parenteral administration (e.g., for use as a source of phosphate, for addition to large volume intravenous fluids, to prevent or correct hypophosphatemia, or for use as an additive in total parenteral fluid formulas).

In some exemplary embodiments, the phosphate salts composition of the present disclosure is a solution comprising or consisting essentially of Water for Injection, about 224 mg/mL monobasic potassium phosphate, and about 236 mg/mL dibasic potassium phosphate, wherein the monobasic potassium phosphate and the dibasic potassium phosphate are formed in situ, and wherein the solution contains less than about 250 µg/L of aluminum. In preferred embodiments, the potassium phosphates solution contains less than about 200 µg/L of aluminum, less than about 150 µg/L of aluminum, or less than about 100 µg/L of aluminum. The phosphate salts solution is devoid of visible particulate matter. The phosphate salts solution may be sterile. The phosphate salts solution is diluted prior to use by parenteral administration (e.g., for use as a source of phosphate, for addition to large volume intravenous fluids, to prevent or correct hypophosphatemia, or for use as an additive in total parenteral fluid formulas).

The phosphate salts compositions or solutions disclosed herein may be dispensed and packaged into a container. Suitable containers can be made of a variety of materials including but not limited to glass and plastic, and may be lined or unlined. In some embodiments, a phosphate salts composition disclosed herein is packaged into a glass vial having a thin layer of silica on the interior surface (e.g., silica-lined vials). In other embodiments, a phosphate salts composition disclosed herein is packaged into plastic vials made of cyclic olefin copolymer (COC) or other suitable medical grade plastics. A container may contain about 4 mL, about 5 mL, about 6 mL, about 7 mL, about 8 mL, about 9 mL, 10 mL, about 11 mL, about 12 mL, about 13 mL, about 14 mL, about 15 mL, about 16 mL, about 17 mL, about 18 mL, about 19 mL, about 20 mL, about 25 mL, about 30 mL, about 35 mL, about 40 mL, about 45 mL, about 50 mL, or about 55 mL of the phosphate salts composition or solution. In specific embodiments, the container (e.g., vial) contains about 10 mL to about 20 mL, about 10 mL to about 15 mL, about 15 mL to about 20 mL of phosphate salts composition or solution. For example, a 20 mL vial may contain about 16 mL of a phosphate salts composition comprising 3 mM/mL total phosphorus in Water for Injection adjusted to a pH of about 5 to about 7. In certain embodiments, more than one container (e.g., vial) comprising the phosphate salts composition or solution is packaged together for distribution. For example, a package may comprise from 1 to about 25 20-mL vials of phosphate salts composition or solution as disclosed herein. As another example, a package may comprise from 1 to about 25 50-mL vials of phosphate salts composition or solution as disclosed herein. In some embodiments, a package may comprise 1, or 5, or 10, or 20 or 25 vials of phosphate salts composition or solution as disclosed herein.

The phosphate salts compositions or solutions, when dispensed into containers as described above, are stable for at least 1 month, at least 3 months, at least 6 months, at least 9 months, at least 12 months, at least 18 months, at least 22 months, or at least 24 months when stored at 25° C. and 40% relative humidity or at 40° C. and 25% relative humidity. A "stable composition" has an amount or level of a critical attribute that does not substantially change over time, and the composition remains free of visible particulate matter. Critical attributes for compositions of the present disclosure may include but are not limited to amount of total phosphorus, amount and/or ratio of phosphate salts, and amount of aluminum. For instance, sodium phosphates compositions or solutions may be referred to as "substantially stable" when the level of aluminum varies by less than 100 µg/L, less than 50 µg/L, or less than 25 µg/L after (a) storage for 18 months at 25° C./40% RH, and/or (b) storage for 24 months at 25° C./40% RH. Potassium phosphates compositions or solutions may be referred to as "substantially stable" when the level of aluminum varies by less than 200 µg/L, less than 150 µg/L, less than 100 µg/L, or less than 90 µg/L after (a) storage for 18 months at 25° C./40% RH, and/or (b) storage for 24 months at 25° C./40% RH. Per USP guidelines, the labeled amount of total phosphorus and the labeled amount of each phosphate salt may deviate by plus or minus five percent for phosphates solutions for parenteral injection. For example, a solution of Sodium Phosphates Injection labeled with a concentration of 3 mM P/mL may contain 2.85 mM P/mL to 3.15 mM P/mL. In some embodiments of the present disclosure, the labeled amount of total phosphorus and the amount of each phosphate salt may deviate by ±3%.

The phosphate salts compositions or solutions provided herein may be formulated in a variety of dosage forms. Suitable dosage forms include injectable formulations, or oral formulations. In some embodiments, the injectable formulation may be for parenteral administration, e.g., intravenous, intramuscular, intrathecal, and the like. In further embodiments, the injectable formulation may be for intravenous administration. In still further embodiments, the formulations are provided in an infusion container (a glass vial, or a polymeric container such as an infusion bag or a blow-fill-seal manufactured plastic container) of 50 mL, 100 mL, 200 mL, 250 mL, 500 mL, 1000 mL, 2000 mL, 3000 mL, or 5000 mL. For example, formulations in the said containers are prepared by diluting any of the phosphate ion concentrations mentioned above, i.e., 1 mM P/mL to about 30 mM P/mL. Thus, the final concentrations of the phosphate ion may range from 1/5000 to 1/50; 2/5000 to 2/50; 3/5000 to 3/50; 4/5000 to 4/50; 5/5000 to 5/50; 6/5000 to 6/50; 7/5000 to 7/50; 8/5000 to 8/50; 9/5000 to 9/50; or 10/5000 to 10/50. The polymeric container may be made of polypropylene, PVC, and the like, or mixtures thereof and the like. Such polymeric containers are known in the art and are widely used in the infusion practice. The equipment to manufacture the containers, and the equipment to fill such containers with the drug product are also known in the pharmaceutical arts.

III. Process for Preparing Phosphate Salts Compositions

Another aspect of the present disclosure encompasses processes for preparing the phosphate salts compositions disclosed herein, which all comprise in situ formed phosphate salts. The process comprises dissolving ortho-phosphoric acid (o-phosphoric acid) and a cationic base in a pharmaceutically acceptable carrier. The resulting solution, referred to as a "bulk solution", may be filter sterilized to form a filtered bulk solution. The bulk solution or the filtered bulk solution may also be dispensed into containers (e.g., vials), which are then sealed and may be stored at room temperature (or colder) for extended periods of time. All steps of the process generally are performed at ambient (e.g., room) temperature. The various steps of the process may be performed under nitrogen (or other inert gas) flow but the use of an inert gas flow is not required. The choice of cationic base is determined by the desired phosphate salts. For example, sodium hydroxide is used for sodium phosphate salts, potassium hydroxide for potassium phosphate salts, etc. In some embodiments, the process does not use any phosphate salt as a starting material. In preferred embodiments, the pharmaceutically acceptable carrier is Water for Injection.

O-phosphoric acid and cationic base are added in amounts needed to achieve the desired amount and ratio of phosphate salts. Generally, stoichiometric amounts of o-phosphoric acid and cationic base are added. For instance, when the phosphate salts are monobasic sodium phosphate and dibasic sodium phosphate, o-phosphoric acid and sodium hydroxide may be added in amounts to achieve a stoichiometry concentration of 3 mmol/mL total phosphorus and 4 mEq $Na^+$/ml, respectively. In another example, the phosphate salts are monobasic potassium phosphate and dibasic potassium phosphate, and o-phosphoric acid and potassium hydroxide may be added in amounts to achieve a stoichiometry concentration of 3 mmol/mL total phosphorus and 4.4 mEq ml, respectively. If the incorrect stoichiometric amount of each starting material is added, the pH of the bulk solution and the amount of each phosphate salt will be adversely affected. This creates a need for stoichiometric accuracy in the quantity of the starting materials. Accordingly, o-phosphoric acid and cationic base are assayed prior to use and the quantities of each adjusted by the assay results. Phosphoric acid is assayed as specified in the USP monograph (i.e., Titration for assay) and the cationic base is assayed as specified in the respective USP monograph (i.e., total alkali). Existence of ionic impurities in the phosphoric acid and cationic base may interfere with the accuracy of the cation amount and the phosphate amount added to a batch, which may lead to out-of-specification results by impacting the ratios among the cation (e.g., $Na^+$, $K^+$), $H_2PO_4^-$, $HPO_4^{2-}$, and $PO_4^{3-}$, as well as the pH and osmolarity of the product. Therefore, the starting materials—e.g., o-phosphoric acid, cationic base, and pharmaceutically acceptable carrier—are USP grade or meet the requirements of the USP even if not labeled as such, and have concentrations of elemental impurities below the limits set in USP <232>, which are reproduced in Table A. In various embodiments, the o-phosphoric acid is an aqueous solution with <1000 ppb of each of the elemental impurities in Table A and the cationic base is a concentrated solution (e.g., about 10N or greater) or solid (e.g., 95.0-100.5%) with <1000 ppb of each of the elemental impurities in Table A. In a specific embodiment, the ortho-phosphoric acid is an 85% aqueous solution as described in Table A or an aqueous 85% aqueous solution with one or more elemental impurities 2-fold, 5-fold, or 10-fold less than said solution of Table A, and the cationic base is a solid (95.0-100.5% or even 98.0-100.5%) as described in Table A or a solid with one or more elemental impurities 2-fold, 5-fold, or 10-fold less than said solution of Table A. Thus, the ortho-phosphoric acid is an 85% aqueous solution of very high purity.

TABLE A

| Element | USP <232>* Class | Concen (µg/g) | Exemplary Embod., Phosphoric acid (85%) Max. concentration | Exemplary Embod., Cationic Base Max. concentration |
|---|---|---|---|---|
| Cadmium | 1 | 0.2 | 200 ppb | 200 ppb |
| Lead | 1 | 0.5 | 200 ppb | 500 ppb |
| Arsenic | 1 | 1.5 | 250 ppb | 1500 ppb |
| Mercury | 1 | 0.3 | 20 ppb | 300 ppb |
| Cobalt | 2A | 0.5 | 200 ppb | 500 ppb |
| Vanadium | 2A | 1 | 200 ppb | 1000 ppb |
| Nickel | 2A | 2 | 250 ppb | 2000 ppb |
| Thallium | 2B | 0.8 | 200 ppb | 800 ppb |
| Gold | 2B | 10 | 200 ppb | 10,000 ppb |
| Palladium | 2B | 1 | 1000 ppb | 1000 ppb |
| Iridium | 2B | 1 | 1000 ppb | 1000 ppb |
| Osmium | 2B | 1 | 1000 ppb | 1000 ppb |
| Rhodium | 2B | 1 | 1000 ppb | 1000 ppb |
| Ruthenium | 2B | 1 | 1000 ppb | 1000 ppb |
| Selenium | 2B | 8 | 1000 ppb | 8000 ppb |
| Silver | 2B | 1 | 100 ppb | 1000 ppb |
| Platinum | 2B | 1 | 100 ppb | 1000 ppb |
| Lithium | 3 | 25 | 100 ppb | 25,000 ppb |
| Antimony | 3 | 9 | 1000 ppb | 9,000 ppb |
| Barium | 3 | 70 | 100 ppb | 70,000 ppb |
| Molybdenum | 3 | 150 | 100 ppb | 150,000 ppb |
| Copper | 3 | 30 | 100 ppb | 30,000 ppb |
| Tin | 3 | 110 | 100 ppb | 60,000 ppb |
| Chromium | 3 | 60 | 100 ppb | 110,000 ppb |

*Permitted Concentrations of Elemental Impurities for Individual Component

In some embodiments, the process comprises charging Water for Injection into a mixing vessel (e.g., mixing bag, stainless steel vessel, etc.) and then dissolving o-phosphoric acid and a cationic base in the Water for Injection to obtain a clear solution. In specific embodiments, the cationic base is sodium hydroxide or potassium hydroxide. The staring materials may be aqueous solutions (e.g., 85% o-phosphorous acid or a concentrated basic solution, such as a 6N-10N solution of NaOH or KOH) or pure materials (e.g., NaOH or KOH pellets). In one example, the o-phosphoric acid is added to create a first admixture and the first admixture is mixed to achieve complete dissolution, and then the cationic base is added to create a second admixture and the second admixture is mixed to achieve complete dissolution. In another example, the cationic base is added to create a first admixture and the first admixture is mixed to achieve complete dissolution, and then the o-phosphoric acid is added to create a second admixture and the second admixture is mixed to achieve complete dissolution. In still other embodiments, the second starting material (whether o-phosphoric acid or the cationic base) may be added before the first starting material is completely dissolved. In embodiments where the cationic base is potassium hydroxide, it is preferable to add the potassium hydroxide first and mix to achieve complete dissolution prior to the addition of o-phosphoric acid.

Upon complete dissolution of the o-phosphoric acid and cationic base, the pH of the clear solution may be monitored, and the pH may be adjusted by the addition of a cationic base. However, pH adjustment of the solution is not needed when stoichiometric amounts of o-phosphoric acid and cationic base are used. The volume (or weight) of the clear solution may be adjusted such that the final concentration of total phosphorus is at the desired level. For example, additional Water for Injection may be added to the clear solution to achieve the final volume, thereby producing a bulk solution. Volume make-up does not affect pH or the molar ratio of the in situ formed phosphate salts.

The pharmaceutical carrier used in the processes disclosed herein may be added cold and/or may be chilled once in the mixing vessel. In specific embodiments, the temperature of the Water for Injection, prior to the addition of a starting material, is about 45° C. or less (e.g., about 40° C. or less, about 35° C. or less, about 30° C. or less, about 25° C. or less, about 20° C. or less, about 15° C. or less, etc.). O-phosphoric acid and a cationic base are then dissolved in the Water for Injection. To control the temperature of the reaction, if desired, the starting material added second may be added in increments until the total amount is achieved. In some examples, the addition of each increment may also require the temperature of the admixture/solution to be no more than about 50° C., no more than about 45° C., no more than about 44° C., no more than about 43° C., no more than about 42° C., no more than about 41° C., or no more than about 40° C. Controlling the temperature of the reaction may be important if high temperatures damage the mixing vessel and/or increases leachables from the mixing vessel to an unacceptable level. In a specific embodiment, the reaction temperature is controlled to not exceed about 60° C., and/or new additions of each increment of the second starting material (often a cationic base) are not made if the temperature of the admixture/solution exceeds 45° C., and/or the solution is cooled to a temperature of 30° C. after all the starting material is dissolved.

Mixing is generally continuous, commencing with the addition of the pharmaceutically acceptable carrier and ceasing prior to filter sterilization or container filling. Pauses in the mixing to allow for the addition of a starting material and/or to sample the solution for in-process testing may occur. The duration of mixing after the addition of a starting material may vary depending upon, for example, the solubility of the starting material, the volume of the mixture, and the like. The duration of mixing is generally just long enough to ensure complete dissolution of the starting material (e.g., o-phosphoric acid or cationic base), resulting in formation of a clear solution by visual inspection. Complete dissolution may also be confirmed by sampling multiple locations within the mixing vessel and testing the samples for pH and/or monobasic/dibasic assay. Extended mixing times may lead to increased levels of dissolved oxygen in the resulting solution. The mixture may be mixed by stirring with a mixing blade or paddle. The rate of stirring can and will vary depending upon, for example, the concentration of starting materials, the volume of the mixture, and so forth. In specific embodiments where the pharmaceutically acceptable carrier is saline, appropriate amount of sodium chloride is added to the said cooled phosphates bulk solution and thoroughly mixed. Methods of preparing such saline admixtures are well-known in the pharmaceutical arts.

In some embodiments, processes of the present disclosure comprise a filtration step, wherein the bulk solution is passed through at least one 0.2 µm filter. The filtration step may reduce the bioburden level in the phosphates salt solution and sterilize the solution. The filter may comprise polyvinylidene difluoride (PVDF), polyethersulfone (PES), cellulose nitrate, cellulose acetate or nylon. In specific embodiments, step (c) comprises serial filtration through two PES 0.2 µm filters. The filtration step may or may not be performed under nitrogen flow (or other inert gas).

The final step comprises dispensing the filtered phosphate salts solution into containers, sealing the containers, and optionally terminally sterilizing the sealed containers. In general, the filtered phosphate salts solution is dispensed into glass vials (optionally silica lined) or plastic vials made of cyclic olefin copolymer (COC) or other medical grade plastic. The size or capacity of the vials may vary, and the volume of filtered phosphate salts solution dispensed into a vial may vary. In various embodiments, the volume of solution dispensed in a vial may be about 4 mL, about 6 mL, about 10 mL, about 15 mL, about 16 mL, about 17 mL, about 18 mL, about 19 mL, about 20 mL, about 30 mL, about 40 mL, or about 50 mL. In specific embodiments, vials are filled with about 16 mL of the filtered phosphate salts solution. The filling may or may not be performed under nitrogen flow (or other inert gas). Once filled with the appropriate volume, the phosphate salts solution may be overlaid with nitrogen or other inert gas, and then the vial is sealed using conventional means. For example, the vial may be sealed with a cap, e.g., a cap comprising a pierceable septum. The filled vials generally are inspected to confirm the correct fill volume, check integrity of the sealing system, and confirm absence of particulates. Vials not meeting these criteria are rejected. Vials meeting these criteria may be terminally sterilized. In preferred embodiments, methods of the present disclosure comprise at least one sterilization step selected from filter sterilization and terminal sterilization. In specific embodiments, methods of the present disclosure comprise a filter sterilization step and a terminal sterilization step.

The final vials that pass inspection may be packaged in multi-unit packages. For example, 1-25 20 mL or 50 mL vials may be packaged into one package. Different numbers of vials and different sized vials can readily be packaged into multi-unit packages.

Another aspect of the present disclosure encompasses a system comprising (a) a composition comprising or consisting essentially of ortho-phosphoric acid, sodium hydroxide, and Water for Injection, wherein the ortho-phosphoric acid and sodium hydroxide are in stoichiometric concentrations of 3 mmol P/mL and 4 mEq Na+/mL, respectively, and the composition contains less than 250 µg/L of aluminum, (b) a mixing vessel containing the composition of (a), and (c) an apparatus operable to cool the composition in the mixing vessel. In some embodiments, the composition contains less than 1000 µg/L of aluminum, less than 500 µg/L of aluminum, less than 250 µg/L of aluminum, or less than 200 µg/L of aluminum. In some embodiments, the composition contains less than 150 µg/L of aluminum, less 100 µg/L of aluminum, less 50 µg/L of aluminum, or even less than 40 µg/L of aluminum (e.g., 20 µg/L or less, 19 µg/L or less, 18 µg/L or less, 17 µg/L or less, 16 µg/L or less, etc.). Suitable compositions are described in Section II, and suitable forms of o-phosphoric acid and sodium hydroxide are described above. Suitable mixing vessels for preparing liquid pharmaceutical compositions are known in the art. In various embodiments, the mixing vessel may be a single-use mixing bag or a stainless steel tank, optionally with one or more sampling ports in addition to the primary opening of the vessel. The size of mixing vessel can vary. In certain embodiments, the mixing vessel may have a volume that is at least about 50 L (e.g., about 50 L, about 100 L, about 150 L, or more). The system is not limited to any one particular apparatus operable to cool the composition in the mixing vessel; any suitable apparatus known in the pharmaceutical arts may be used, including but not limited to a variety of cooling jackets, coils, or pipes that position cooling elements on the sides and/or end(s) of the mixing vessel to facilitate heat transfer (e.g., conventional/single external jacket, half coil jacket, dimple jackets, plate coils, constant flux cooling jacket, etc.). In one example, the apparatus operable to cool the composition in the mixing vessel is a cooling jacket. In a specific embodiment, the system comprises a jacketed mixing container. In various embodiments, the composition in the mixing vessel may be cooled to a temperature of about 60° C. or less. For instance, the temperature may be about 55° C. or less, about 50° C. or less, about 45° C. or less, about 40° C. or less, about 35° C. or less, about 30° C. or less, about 25° C. or less, about 20° C. or less. In further examples, the temperature may be about 15° C. to about 60° C., or about 15° C. to about 50° C.

Yet another aspect of the present disclosure encompasses a system comprising (a) a composition comprising or consisting essentially of ortho-phosphoric acid, sodium hydroxide, and Water for Injection, wherein the ortho-phosphoric acid and potassium hydroxide are in stoichiometric concentrations of 3 mmol P/mL and 4.4 mEq K+/mL, respectively, and the composition contains less than 1500 µg/L of aluminum, (b) a mixing vessel containing the composition of (a), and (c) an apparatus operable to cool the composition in the mixing vessel. In some embodiments, the composition contains less than 1000 µg/L of aluminum, less than 500 µg/L of aluminum, less than 250 µg/L of aluminum, less than 200 µg/L of aluminum, less than 150 µg/L of aluminum, or less 100 µg/L of aluminum. Suitable forms of o-phosphoric acid and potassium hydroxide are described above. Suitable mixing vessels for preparing pharmaceutical solutions are known in the art. In various embodiments, the mixing vessel may be a single-use mixing bag or a stainless steel tank, optionally with one or more sampling ports in addition to the primary opening of the vessel. The size of mixing vessel can vary. In certain embodiments, the mixing vessel may have a volume that is at least about 50 L (e.g., about 50 L, about 100 L, about 150 L, or more). The system is not limited to any one particular apparatus operable to cool the composition in the mixing vessel; any suitable apparatus known in the pharmaceutical arts may be used, including but not limited to a variety of cooling jackets, coils, or pipes that position cooling elements on the sides and/or end(s) of the mixing vessel to facilitate heat transfer (e.g., conventional/single external jacket, half coil jacket, dimple jackets, plate coils, constant flux cooling jacket, etc.). In one example, the apparatus operable to cool the composition in the mixing vessel is a cooling jacket. In a specific embodiment, the system comprises a jacketed mixing container. In various embodiments, the composition in the mixing vessel may be cooled to a temperature of about 60° C. or less. For instance, the temperature may be about 55° C. or less, about 50° C. or less, about 45° C. or less, about 40° C. or less, about 35° C. or less, about 30° C. or less, about 25° C. or less, about 20° C. or less. In further examples, the temperature may be about 15° C. to about 60° C., or about 15° C. to about 50° C.

IV. Methods of Using Phosphate Salts Compositions

Still another aspect of the present disclosure encompasses methods of using phosphate salts compositions disclosed herein to provide phosphorous to individuals in need thereof. The disclosed phosphate salts compositions may be used to prevent or correct hypophosphatemia in patients in need thereof (e.g., adults, pediatric patients, and infants when oral or enteral replacement is not possible, insufficient or contraindicated). In these methods, an injectable composition is prepared by aseptically diluting a phosphate salts composition described herein with a saline solution (e.g., 0.9% Sodium Chloride Injection, USP) or a dextrose solution (e.g., 5% Dextrose Solution, USP). The injectable composition is then administered to the individual in need thereof. Alternatively, the disclosed phosphate salts compositions may be used as an additive to parenteral nutrition formulations for patients in need thereof (e.g., adults, pediatric patients, and infants when oral or enteral nutrition is not possible, insufficient, or contraindicated). In these methods, an injectable composition is prepared by aseptically admixing a phosphate salts composition described herein with a parenteral nutrition formulation. The injectable composition is then administered to the individual in need thereof.

In general, the phosphate salts compositions disclosed herein can be used to meet phosphorous nutritional requirements in individuals with hypophosphatemia or in individuals receiving total parenteral nutrition. In general, diluted phosphate salts compositions, or phosphate salts compositions admixed with a parenteral nutrition formulation, are administered intravenously (e.g., via peripheral or central venous infusion). The diluted solution or admixture may be inspected visually for particulate matter and discoloration prior to administration. The diluted solution or admixture may be refrigerated until ready for use and typically would be used within 24 hours of dilution or mixing. The dose of phosphorous can vary and are dependent, for example, on the individual needs of the patient (e.g., to correct hypophosphatemia or for parenteral nutrition, the age and/or weight of the individual, renal function, etc.) and/or the route of administration (e.g., central or peripheral venous infusion). The patient's serum inorganic phosphates should be monitored as a guide to dosage. The normal level of serum inorganic phosphate is 3 to 4.5 mg/100 mL in adults and 4 to 7 mg/100 mL in children. Serum calcium, magnesium, potassium and/or sodium concentration may also be monitored as a guide to dosage. Renal function is also a consideration—patients with moderate renal impairment typically start at the low end of a dosage range. Those skilled in the art are familiar with means for administration as well as means for determining the rate of administration.

In some embodiments, about 10 to 15 mmol of phosphorous (equivalent to 310 to 465 mg elemental phosphorous) per liter bottle of total parenteral nutrition (TPN) solution is adequate to maintain normal serum phosphate in patients on TPN, though larger amounts may be required in hypermetabolic states. The amount of the phosphate counter ion should be kept in mind, and if necessary, serum levels of the counter ion should be monitored. The suggested dose of phosphorous for infants receiving TPN is 1.5 to 2 mmol P/kg/day.

In some embodiments, the dose of phosphorous may be as indicated in Table B or Table C.

TABLE B

Recommended Initial or Single Dose of Potassium Phosphates Injection in Intravenous Fluids to Correct Hypophosphatemia in Adults and Pediatric Patients 12 Years of Age and Older

| Serum Phosphorous Concentration | Phosphorous Dosage | Corresponding Potassium Content |
|---|---|---|
| 1.8 mg/dL to 2.4 mg/dL | 0.16 mmol/kg to 0.31 mmol/kg | 0.25 mEq/kg to 0.49 mEq/kg of potassium |
| 1 mg/dL to 1.7 mg/dL | 0.32 mmol/ kg to 0.43 mmol/kg | 0.5 mEq/kg to 0.68 mEq/kg of potassium |

TABLE B-continued

Recommended Initial or Single Dose of Potassium Phosphates Injection in Intravenous Fluids to Correct Hypophosphatemia in Adults and Pediatric Patients 12 Years of Age and Older

| Serum Phosphorous Concentration | Phosphorous Dosage | Corresponding Potassium Content |
| --- | --- | --- |
| Less than 1 mg/dL | 0.44 mmol/kg to 0.64 mmol/kg | 0.69 mEq/kg to 1 mEq/kg of potassium |

TABLE C

Recommended Initial or Single Dose of Potassium Phosphates Injection in Intravenous Fluids to Correct Hypophosphatemia in Adults and Pediatric Patients 12 Years of Age and Older

| Patient Population | Generally Recommended Phosphorous Daily Dosage (Potassium Content) |
| --- | --- |
| Adults weighing at least 45 kb Pediatric patients 12 years or age and older weighing at least 40 kg | 20 mmol/day to 40 mmol/day (31 mEq/day to 62.7 mEq/day) |

V. Numbered Embodiments

Embodiment 1. A solution for parenteral administration comprising in situ formed phosphate salts in a pharmaceutically acceptable carrier, wherein the solution contains less than about 250 µg/L of aluminum.

Embodiment 2. The solution of embodiment 1, wherein the in situ formed phosphate salts provide about 3 millimoles/mL total phosphorus.

Embodiment 3. The solution of embodiment 1 or embodiment 2, wherein the solution contains less than about 200 µg/L of aluminum.

Embodiment 4. The solution of embodiment 1 or embodiment 2, wherein the solution contains less than about 150 µg/L of aluminum.

Embodiment 5. The solution of embodiment 1 or embodiment 2, wherein the solution contains less than about 100 µg/L of aluminum.

Embodiment 6. The solution of embodiment 1 or embodiment 2, wherein the solution contains less than about 50 µg/L of aluminum.

Embodiment 7. A solution comprising phosphate salts in an amount that provides about 3 millimoles/mL total phosphorus and a pharmaceutically acceptable carrier, wherein the solution contains less than 17 µg/L of aluminum.

Embodiment 8. The solution of any one of embodiments 1 to 7, wherein the solution contains about 3 millimoles/mL total phosphorus.

Embodiment 9. A solution consisting essentially of phosphate salts in an amount that provides about 3 millimoles/mL total phosphorus and a pharmaceutically acceptable carrier, wherein the solution contains less than 17 µg/L of aluminum.

Embodiment 10. The solution of any one of embodiments 1 to 9, wherein the solution contains no more than 16 µg/L of aluminum.

Embodiment 11. The solution of any one of embodiments 1 to 9, wherein the solution contains about 4 µg/L to about 16 µg/L of aluminum.

Embodiment 12. The solution of any one of embodiments 1 to 11, wherein the solution has a pH of about pH 5 to about pH 9.

Embodiment 13. The solution of any one of embodiments 1 to 12, wherein the pharmaceutically acceptable carrier is Water for Injection or a dextrose solution.

Embodiment 14. The solution of any one of embodiments 1 to 13, wherein the phosphate salts are formed in situ by reacting phosphoric acid with strong anionic base.

Embodiment 15. The solution of any one of embodiments 1 to 14, wherein the phosphate salts are sodium phosphate salts or potassium phosphate salts, and wherein the compositions are not stored under refrigeration.

Embodiment 16. The solution of embodiment 15, wherein the phosphates are formed in situ by reacting phosphoric acid with sodium hydroxide or potassium hydroxide.

Embodiment 17. The solution of 16, wherein the phosphate salts are monobasic sodium phosphate and dibasic sodium phosphate.

Embodiment 18. The solution of embodiment 17 wherein the solution has a pH of about pH 5 to about pH 9.

Embodiment 19. The solution of embodiment 17, wherein the solution has a pH of about pH 5 to about pH 6.

Embodiment 20. The solution of embodiment 17, wherein the solution has a pH of about pH 5.4 to about pH 5.6.

Embodiment 21. The solution of embodiment 17, wherein the solution has a pH of greater than pH 5.4 to about pH 5.6.

Embodiment 22. The solution of 21, wherein the phosphate salts are monobasic potassium phosphate and dibasic potassium phosphate.

Embodiment 23. The solution of embodiment 22, wherein the solution has a pH of about pH 5 and about pH 9.

Embodiment 24. The solution of embodiment 22, wherein the solution has a pH of about pH 6 to about pH 8.

Embodiment 25. The solution of embodiment 22, wherein the solution has a pH of about pH 6.5 to about pH 7.5 or a pH of about pH 6.2 to pH 6.8.

Embodiment 26. The solution of any one of embodiments 1 to 25, wherein the solution is devoid of visual particulate matter when stored for at least 12 months (e.g. 12, 13, 14, 15, 16, 17, 18 months or longer) at 25° C. and 40% relative humidity.

Embodiment 27. The solution of any one of embodiments 1 to 25, wherein the solution is packaged in a sealed glass container, and wherein the compositions are not stored under refrigeration.

Embodiment 28. The solution of embodiment 27, wherein the glass container is silica-lined.

Embodiment 29. The solution of any one of embodiments 1 to 19, wherein the solution is packaged in a sealed plastic container, and wherein the compositions are not stored under refrigeration.

Embodiment 30. The solution of any one of embodiments 21 to 23, wherein the solution is devoid of visual particulate matter and the solution contains less than 17 µg/L of aluminum, at the time of packaging and/or after terminal sterilization.

Embodiment 31. The solution of any one of embodiments 21 to 23, wherein the solution is devoid of visual particulate matter and the solution contains no more than 16 µg/L of aluminum, at the time of packaging and/or after terminal sterilization.

Embodiment 32. The solution of any one of embodiments 21 to 23, wherein the solution is devoid of visual particulate matter and the solution contains less than 17 µg/L of aluminum, after the packaged container is stored for at least 12 months (e.g., 12, 13, 14, 15, 16, 17, 18 months or longer) at 25° C. and 40% relative humidity.

Embodiment 33. The solution of any one of embodiments 21 to 23, wherein the solution is devoid of visual particulate matter and the solution contains no more than 16 µg/L of aluminum, after the packaged container is stored for at least 12 months (e.g., 12, 13, 14, 15, 16, 17, 18 months or longer) at 25° C. and 40% relative humidity.

Embodiment 34. A solution comprising salts of potassium and phosphate in an amount that provides about 3 millimoles/mL total phosphorus and about 4.4 mEq/mL potassium, a pharmaceutically acceptable carrier, and less than about 250 µg/L of aluminum.

Embodiment 35. The solution of embodiment 28, wherein the solution has about 3 millimoles/mL total phosphorus.

Embodiment 36. A solution consisting essentially of salts of potassium and phosphate in an amount that provides about 3 millimoles/mL total phosphorus and about 4.4 mEq/mL potassium, and a pharmaceutically acceptable carrier, wherein the solution contains less than about 250 µg/L of aluminum.

Embodiment 37. The solution of any one of embodiments 34 to 36, wherein the pharmaceutically acceptable carrier is Water for Injection or a dextrose solution.

Embodiment 38. The solution of any one of embodiments 34 to 37, wherein the salts of potassium phosphate are monobasic potassium phosphate and dibasic potassium phosphate.

Embodiment 39. The solution of embodiment 38, wherein the solution has a pH of about pH 5 to about pH 9.

Embodiment 40. The solution of embodiment 39, wherein the solution has a pH of about pH 6 to about pH 8.

Embodiment 41. The solution of embodiment 39, wherein the solution has a pH of about pH 6.5 to about pH 7.5 or a pH of about pH 6.2 to pH 6.8.

Embodiment 42. A solution comprising monobasic potassium phosphate and dibasic potassium phosphate in a molar ratio about 1.2 to about 1, Water for Injection, and less than about 200 µg/L of aluminum, wherein the solution has a pH of about 6.2 to about 6.8.

Embodiment 43. A solution consisting essentially of monobasic potassium phosphate and dibasic potassium phosphate in a molar ratio about 1.2 to about 1, and Water for Injection, wherein the solution contains less than 200 µg/L of aluminum and a pH of about 6.2 to about 6.8.

Embodiment 44. The solution of embodiment 42 or 43, wherein the solution has about 3 millimoles/mL total phosphorus.

Embodiment 45. A solution comprising Water for Injection, about 175 mg/mL monobasic potassium phosphate, about 300 mg/mL dibasic potassium phosphate, less than about 250 µg/L of aluminum, and a pH of about 6.2 to about 6.8.

Embodiment 46. A solution consisting essentially of Water for Injection, about 175 mg/mL monobasic potassium phosphate, and about 300 mg/mL dibasic potassium phosphate, wherein the solution contains less than about 250 µg/L of aluminum and a pH of about 6.2 to about 6.8.

Embodiment 47. The solution of any one of embodiments 34 to 46, wherein the solution contains less than about 200 µg/L of aluminum or less than about 150 µg/L of aluminum.

Embodiment 48. The solution of any one of embodiments 34 to 46, wherein the solution contains less than about 100 µg/L of aluminum.

Embodiment 49. The solution of any one of embodiments 34 to 46, wherein the solution contains less than about 50 µg/L of aluminum.

Embodiment 50. The solution of any one of embodiments 34 to 49, wherein the solution is devoid of visual particulate matter when stored for at least 12 months (e.g., 12, 13, 14, 15, 16, 17, 18 months or longer) at 25° C. and 40% relative humidity.

Embodiment 51. The solution of any one of embodiments 34 to 49, wherein the solution is packaged in a sealed glass container.

Embodiment 52. The solution of embodiment 51, wherein the glass container is silica-lined.

Embodiment 53. The solution of any one of embodiments 34 to 49, wherein the solution is packaged in a sealed plastic container.

Embodiment 54. The solution of any one of embodiments 51 to 53, wherein the solution is devoid of visual particulate matter and the solution contains less than 250 µg/L of aluminum, at the time of packaging and/or after the container is terminally sterilized.

Embodiment 55. The solution of any one of embodiments 51 to 53, wherein the solution is devoid of visual particulate matter and the solution contains less than 250 µg/L of aluminum, after the container is stored for at least 12 months (e.g., 12, 13, 14, 15, 16, 17, 18 months or longer) at 25° C. and 40% relative humidity.

Embodiment 56. The solution of embodiment 54 or 55, wherein the solution contains less than 200 µg/L of aluminum or less than 150 µg/L of aluminum.

Embodiment 57. The solution of embodiment 54 or 55, wherein the solution contains less than 100 µg/L of aluminum.

Embodiment 58. The solution of embodiment 54 or 55, wherein the solution contains less than 50 µg/L of aluminum.

Embodiment 59. The solution of any one of embodiments 34 to 58, wherein the potassium phosphate salts are formed in situ by reacting phosphoric acid with potassium hydroxide.

Embodiment 60. A solution comprising salts of sodium and phosphate in an amount that provides about 3 millimoles/mL total phosphorus and about 4 mEq/mL sodium, a pharmaceutically acceptable carrier, and less than 17 µg/L of aluminum.

Embodiment 61. The solution of embodiment 60, wherein the solution contains about 3 millimoles/mL total phosphorus.

Embodiment 62. A solution consisting essentially of salts of sodium and phosphate in an amount that provides about 3 millimoles/mL total phosphorus and about 4 mEq/mL sodium, and a pharmaceutically acceptable carrier, wherein the solution contains less than 17 µg/L of aluminum.

Embodiment 63. The solution of any one of embodiments 60 to 62, wherein the pharmaceutically acceptable carrier is Water for Injection or a dextrose solution.

Embodiment 64. The solution of any one of embodiments 60 to 63, wherein the salts of sodium phosphate are monobasic sodium phosphate and dibasic sodium phosphate.

Embodiment 65. The solution of embodiment 64, wherein the solution has a pH of about pH 5 to about pH 9.

Embodiment 66. The solution of embodiment 64, wherein the solution has a pH of about pH 5 to about pH 6.

Embodiment 67. The solution of embodiment 64, wherein the solution has a pH of about pH 5.4 to about pH 5.6.

Embodiment 68. The solution of embodiment 64, wherein the solution has a pH of greater than pH 5.4 to about pH 5.6.

Embodiment 69. A solution comprising monobasic sodium phosphate and dibasic sodium phosphate in a molar ratio about 2 to about 1, Water for Injection, and less than 17 µg/L of aluminum, wherein the solution has a pH of about pH 5.4 to about pH 5.6.

Embodiment 70. A solution consisting essentially of monobasic sodium phosphate and dibasic sodium phosphate in a molar ratio about 2 to about 1, and Water for Injection, wherein the solution contains less than 17 μg/L of aluminum and the solution has a pH of about pH 5.4 to about pH 5.6.

Embodiment 71. The solution of embodiment 69 or 70, wherein the solution contains about 3 millimoles/mL total phosphorus.

Embodiment 72. A solution comprising Water for Injection, about 240 mg/mL monobasic sodium phosphate, about 142 mg/mL dibasic sodium phosphate, less than 17 μg/L of aluminum, and a pH from about 5.4 to about 5.6.

Embodiment 73. A solution consisting essentially of Water for Injection, about 240 mg/mL monobasic sodium phosphate, and about 142 mg/mL dibasic sodium phosphate, wherein the solution contains less than 17 μg/L of aluminum and the solution has a pH from about 5.4 to about 5.6.

Embodiment 74. The solution of any one of embodiments 69 to 73, wherein the pH of the solution is about pH 5.5 to about pH 5.6.

Embodiment 75. The solution of any one of embodiments 60 to 74, wherein the solution contains no more than 16 μg/L of aluminum.

Embodiment 76. The solution of any one of embodiments 60 to 74, wherein the solution contains about 4 μg/L to about 16 μg/L of aluminum.

Embodiment 77. The solution of any one of embodiments 60 to 76, wherein the solution is devoid of visual particulate matter when stored for at least 12 months (e.g., 12, 13, 14, 15, 16, 17, 18 months or longer) at 25° C. and 40% relative humidity.

Embodiment 78. The solution of any one of embodiments 60 to 76, wherein the solution is packaged in a sealed glass container.

Embodiment 79. The solution of embodiment 78, wherein the glass container is silica-lined.

Embodiment 80. The solution of any one of embodiments 60 to 76, wherein the solution is packaged in a sealed plastic container.

Embodiment 81. The solution of any one of embodiments 78 to 80, wherein the solution is devoid of visual particulate matter and contains less than 17 μg/L of aluminum, at the time of packaging and/or after the container is terminally sterilized.

Embodiment 82. The solution of any one of embodiments 78 to 80, wherein the solution contains less than 17 μg/L of aluminum after the container is stored for at least 12 months (e.g., 12, 13, 14, 15, 16, 17, 18 months or longer) at 25° C. and 40% relative humidity, and the solution is devoid of visual particulate matter.

Embodiment 83. The solution of embodiment 81 or 82, wherein the solution contains no more than 16 μg/L of aluminum.

Embodiment 84. The solution of embodiment 81 or 82, wherein the solution contains about 4 μg/L to about 16 μg/L of aluminum.

Embodiment 85. The solution of any one of embodiments 60 to 84, wherein the sodium phosphate salts are formed in situ by reacting phosphoric acid with sodium hydroxide.

Embodiment 86. The solution of any one of the preceding embodiments, wherein the osmolar concentration is about 7 mOsmol/mL.

Embodiment 87. The solution of any one of the preceding embodiments, wherein the solution is suitable for parenteral administration.

Embodiment 88. A solution comprising phosphate salts in an amount that provides about 3 millimoles/mL total phosphorus and a pharmaceutically acceptable carrier, wherein the solution contains less than 250 μg/L of aluminum after storage for at least 12 months (e.g., 12, 13, 14, 15, 16, 17, 18 months or longer) at 25° C. and 40% relative humidity in a sealed container.

Embodiment 89. The solution of embodiment 88, wherein the solution contains about 3 millimoles/mL total phosphorus.

Embodiment 90. A solution consisting essentially of phosphate salts in an amount that provides about 3 millimoles/mL total phosphorus and a pharmaceutically acceptable carrier, wherein the solution contains less than 250 μg/L of aluminum after storage for at least 12 months (e.g., 12, 13, 14, 15, 16, 17, 18 months or longer) at 25° C. and 40% relative humidity in a sealed container.

Embodiment 91. The solution of any one of embodiments 88 to 90, wherein the solution contains less than 100 μg/L of aluminum after storage for at least 12 months (e.g., 12, 13, 14, 15, 16, 17, 18 months or longer) at 25° C. and 40% relative humidity in a sealed container.

Embodiment 92. The solution of any one of embodiments 88 to 90, wherein the solution contains less than 50 μg/L of aluminum after storage for at least 12 months (e.g., 12, 13, 14, 15, 16, 17, 18 months or longer) at 25° C. and 40% relative humidity in a sealed container.

Embodiment 93. The solution of any one of embodiments 88 to 92, wherein the solution has a pH of about pH 5 to about pH 9.

Embodiment 94. The solution of any one of embodiments 88 to 93, wherein the pharmaceutically acceptable carrier is Water for Injection or a dextrose solution.

Embodiment 95. The solution of any one of embodiments 88 to 94, wherein the phosphate salts are formed in situ by reacting phosphoric acid with strong cationic base.

Embodiment 96. The solution of any one of embodiments 88 to 94, wherein the phosphate salts are sodium phosphate salts or potassium phosphate salts.

Embodiment 97. The solution of embodiment 96, wherein the phosphate salts are formed in situ by reacting phosphoric acid with sodium hydroxide or potassium hydroxide.

Embodiment 98. The solution of 97, wherein the phosphate salts are monobasic sodium phosphate and dibasic sodium phosphate.

Embodiment 99. The solution of embodiment 98, wherein the solution has a pH of about pH 5 to about pH 6.

Embodiment 100. The solution of embodiment 98, wherein the solution has a pH of about pH 5.4 to about pH 5.6.

Embodiment 101. The solution of embodiment 98, wherein the solution has a pH of greater than pH 5.4 to about pH 5.6.

Embodiment 102. The solution of 96, wherein the phosphate salts are monobasic potassium phosphate and dibasic potassium phosphate.

Embodiment 103. The solution of embodiment 102, wherein the solution has a pH of about pH 6 to about pH 8.

Embodiment 104. The solution of embodiment 102, wherein the solution has a pH of about pH 6.5 to about pH 7.5 or a pH of about pH 6.2 to pH 6.8.

Embodiment 105. The solution of any one embodiments 88 to 104, wherein the solution has an osmolar concentration of about 7 mOsmol/mL to about 7.5 mOsmol/mL, or preferably about 7.4 mOsmol/mL.

Embodiment 106. The solution of any one embodiments 88 to 105, wherein the solution is suitable for parenteral administration.

Embodiment 107. A solution comprising monobasic sodium phosphate and dibasic sodium phosphate in a molar ratio about 2 to about 1 and Water for Injection, wherein the solution's aluminum content varies by less than 100 µg/L between the time of packaging and after storage for at least 12 months (e.g., 12, 13, 14, 15, 16, 17, 18 months or longer) at 25° C. and 40% relative humidity.

Embodiment 108. The solution of embodiment 107, wherein the aluminum content varies by less than 75 µg/L between the time of packaging and after storage for at least 12 months (e.g., 12, 13, 14, 15, 16, 17, 18 months or longer) at 25° C. and 40% relative humidity.

Embodiment 109. The solution of embodiment 107, wherein the aluminum content varies by less than 50 µg/L between the time of packaging and after storage for at least 12 months (e.g., 12, 13, 14, 15, 16, 17, 18 months or longer) at 25° C. and 40% relative humidity.

Embodiment 110. The solution of embodiment 107, wherein the aluminum content varies by less than 25 µg/L between the time of packaging and after storage for at least 12 months (e.g., 12, 13, 14, 15, 16, 17, 18 months or longer) at 25° C. and 40% relative humidity.

Embodiment 111. The solution of any one of embodiments 107 to 110, wherein the solution has a pH of about pH 5.4 to about pH 5.6 at the time of packaging and after storage for at least 12 months (e.g., 12, 13, 14, 15, 16, 17, 18 months or longer) at 25° C. and 40% relative humidity.

Embodiment 112. The solution of embodiment 111, wherein the solution has a pH of about pH 5.5 to about pH 5.6 at the time of packaging and after storage for at least 12 months (e.g., 12, 13, 14, 15, 16, 17, 18 months or longer) at 25° C. and 40% relative humidity.

Embodiment 113. The solution of any one of embodiments 107 to 112, wherein the solution contains about 3 mM total phosphorus per mL.

Embodiment 114. A solution comprising monobasic potassium phosphate and dibasic potassium phosphate in a molar ratio about 1.2 to about 1 and Water for Injection, wherein the solution's aluminum content varies by less than 200 µg/L between the time of packaging and after storage for at least 12 months (e.g., 12, 13, 14, 15, 16, 17, 18 months or longer) at 25° C. and 40% relative humidity.

Embodiment 115. The solution of embodiment 114, wherein the aluminum content varies by less than 150 µg/L between the time of packaging and after storage for at least 12 months (e.g., 12, 13, 14, 15, 16, 17, 18 months or longer) at 25° C. and 40% relative humidity.

Embodiment 116. The solution of embodiment 114, wherein the aluminum content varies by less than 100 µg/L between the time of packaging and after storage for at least 12 months (e.g., 12, 13, 14, 15, 16, 17, 18 months or longer) at 25° C. and 40% relative humidity.

Embodiment 117. The solution of any one of embodiments 114 to 116, wherein the solution has a pH of about pH 6 to about pH 7 at the time of packaging and after storage for at least 12 months (e.g., 12, 13, 14, 15, 16, 17, 18 months or longer) at 25° C. and 40% relative humidity.

Embodiment 118. The solution of embodiment 117, wherein the solution has a pH of about pH 6.2 to about pH 6.6 at the time of packaging and after storage for at least 12 months (e.g., 12, 13, 14, 15, 16, 17, 18 months or longer) at 25° C. and 40% relative humidity.

Embodiment 119. The solution of any one of embodiments 114 to 118, wherein the solution contains about 3 mM total phosphorus per mL.

Embodiment 120. A sealed container comprising a solution for parenteral administration, wherein the solution is a solution of any one of the preceding embodiments.

Embodiment 121. A method of using a solution of phosphate salts, the method comprising (a) diluting a solution of any one of embodiments 1 to 119; and (b) intravenously administering the diluted solution of phosphate salts to a patient in need thereof.

Embodiment 122. A method of using a solution of phosphate salts, the method comprising (a) diluting a solution of any one of embodiments 34 to 86; and (b) intravenously administering the diluted solution of phosphate salts to a patient in need thereof.

Embodiment 123. A system comprising: (a) a composition comprising or consisting essentially of ortho-phosphoric acid, sodium hydroxide, and Water for Injection, wherein the ortho-phosphoric acid and sodium hydroxide are in stoichiometric concentrations of 3 mmol P/mL and 4 mEq Na+/mL, respectively, and the composition contains less than 250 µg/L of aluminum; (b) a mixing vessel containing the composition of (a); and (c) an apparatus operable to cool the composition in the mixing vessel.

Embodiment 124. The system of embodiment 123 or embodiment 124, wherein the composition of (a) contains less than 200 µg/L of aluminum.

Embodiment 126. The system of embodiment 123 or embodiment 124, wherein the composition of (a) contains less than 175 µg/L of aluminum.

Embodiment 126. The system of embodiment 123 or embodiment 124, wherein the composition contains less than 150 µg/L of aluminum.

Embodiment 127. The system of embodiment 123 or embodiment 124, wherein the composition of (a) contains less 100 µg/L of aluminum.

Embodiment 128. The system of embodiment 123 or embodiment 124, wherein the composition of (a) contains less 50 µg/L of aluminum.

Embodiment 129. The system of embodiment 123 or embodiment 124, wherein the composition of (a) contains or less than 40 µg/L of aluminum.

Embodiment 130. The system of any one of embodiments 123 to 129, wherein the mixing vessel has a volume that is at least about 50 L.

Embodiment 131. The system of embodiment 130, wherein the mixing vessel is a single-use mixing bag or a stainless steel tank.

Embodiment 132. The system of any one of embodiments 123 to 131, wherein the composition in the mixing vessel is cooled to a temperature of about 60° C. or less.

Embodiment 133. A liquid composition comprising ortho-phosphoric acid, a cationic base selected from potassium hydroxide and sodium hydroxide, and Water for Injection, wherein the o-phosphoric acid and cationic base are in an amount that provides about 3 millimoles phosphate per mL and about 4 to about 4.5 mEq of cation (e.g., K+ or Na+) per mL, and wherein the composition contains less than 250 µg/L of aluminum.

Embodiment 134. The composition of embodiment 133, wherein the composition contains less than 200 µg/L of aluminum.

Embodiment 135. The composition of embodiment 133, wherein the composition contains less than 170 µg/L of aluminum.

Embodiment 136. The composition of embodiment 133, wherein the composition less than 150 µg/L of aluminum.

Embodiment 137. The composition of embodiment 133, wherein the composition contains less 100 µg/L of aluminum.

Embodiment 138. The composition of embodiment 133, wherein the composition contains less 50 µg/L of aluminum.

Embodiment 139. The composition of embodiment 133, wherein the composition contains or less than 40 µg/L of aluminum.

Embodiment 140. The composition of any one of embodiments 133 to 139, wherein the composition has a volume that is at least about 50 L.

Embodiment 141. The composition of any one of embodiments 133 to 140, wherein the composition has a temperature of about 60° C. or less.

Embodiment 142. A process for preparing a pharmaceutical solution comprising a monobasic sodium phosphate and dibasic sodium phosphate in a molar ratio of about 2 to about 1, respectively, the method comprising (a) mixing an amount of ortho-phosphoric acid that provides about 3 millimoles phosphorus per mL and an amount of sodium hydroxide that provides about 4 mEq of Na+ per mL in Water for Injection to obtain a clear solution, wherein the clear solution has less than 100 µg/mL of aluminum, and (b) sterilizing the pharmaceutical solution by filter sterilization and/or terminal sterilization.

Embodiment 143. The process of embodiment 142, the method comprising in step (a) mixing an amount of ortho-phosphoric acid that provides about 3 millimoles phosphorus per mL and an amount of sodium hydroxide that provides about 4 mEq of Na+ per mL in Water for Injection to obtain a clear solution, wherein the clear solution has less than 50 µg/mL of aluminum or less than 20 µg/mL of aluminum.

Embodiment 144. A process for preparing a pharmaceutical solution comprising a monobasic potassium phosphate and dibasic potassium phosphate in a molar ratio of about 1.2 to about 1, respectively, the method comprising (a) mixing an amount of ortho-phosphoric acid that provides about 3 millimoles phosphorus per mL and an amount of potassium hydroxide that provides about 4.4 mEq of K+ per mL in Water for Injection to obtain a clear solution, wherein the clear solution has less than 250 µg/mL of aluminum, and (b) sterilizing the pharmaceutical solution by filter sterilization and/or terminal sterilization.

Embodiment 145. The process of embodiment 144, the method comprising in step (a) mixing an amount of ortho-phosphoric acid that provides about 3 millimoles phosphorus per mL and an amount of potassium hydroxide that provides about 4.4 mEq of K+ per mL in Water for Injection to obtain a clear solution, wherein the clear solution has less than 100 µg/mL of aluminum.

Embodiment 146. A solution for parenteral administration comprising or consisting essentially of potassium phosphate salts in a pharmaceutically acceptable carrier, wherein the solution contains less than about 250 µg/L of aluminum and has no more than 0.00309 millimoles of aluminum for every mole of phosphorus.

Embodiment 147. The solution of embodiment 146, wherein the solution contains less than about 250 µg/L of aluminum and has no more than 0.00309 millimoles of aluminum for every mole of phosphorus provided by the potassium phosphate salts.

Embodiment 148. The solution of claim embodiment 146, wherein the solution contains less than about 200 µg/L of aluminum.

Embodiment 149. The solution of embodiment 146, wherein the solution contains less than about 100 µg/L of aluminum.

Embodiment 150. The solution of embodiment 146, wherein the pharmaceutically acceptable carrier is Water for Injection, saline, or a dextrose solution.

Embodiment 151. The solution of embodiment 146, wherein the phosphate salts are formed in situ by reacting phosphoric acid with potassium hydroxide.

Embodiment 152. The solution of embodiment 146, wherein the phosphate salts are monobasic potassium phosphate and dibasic potassium phosphate.

Embodiment 153. The solution of embodiment 152, wherein the solution has a pH of about pH 6 to about pH 8.

Embodiment 154. The solution of embodiment 153, wherein the solution has a pH of about pH 6.5 to about pH 7.5 or a pH of about pH 6.2 to pH 6.8.

Embodiment 155. The solution of embodiment 146, wherein the solution contains less than 250 µg/L of aluminum after storage for at least 12 months (e.g., 12, 13, 14, 15, 16, 17, 18 months or longer) at 25° C. and 40% relative humidity in a sealed container.

Embodiment 156. A solution for parenteral administration comprising or consisting essentially of sodium phosphate salts in a pharmaceutically acceptable carrier, wherein the solution contains less than about 100 µg/L of aluminum and has no more than 0.00124 millimoles of aluminum for every mole of phosphorus provided by the sodium phosphate salts.

Embodiment 157. The solution of embodiment 16, wherein the solution contains less than about 100 µg/L of aluminum and has no more than 0.00124 millimoles of aluminum for every mole of phosphorus in the solution.

Embodiment 158. The solution of claim embodiment 156, wherein the solution contains less than about 50 µg/L of aluminum.

Embodiment 159. The solution of embodiment 156, wherein the solution contains less than about 25 µg/L of aluminum.

Embodiment 160. The solution of embodiment 156, wherein the solution contains less than 17 µg/L of aluminum.

Embodiment 161. The solution of embodiment 156, wherein the solution contains no more than 16 µg/L of aluminum.

Embodiment 162. The solution of embodiment 156, wherein the solution contains about 4 µg/L to about 16 µg/L of aluminum.

Embodiment 163. The solution of embodiment 156, wherein the pharmaceutically acceptable carrier is Water for Injection, saline, or a dextrose solution.

Embodiment 164. The solution of embodiment 156, wherein the phosphate salts are formed in situ by reacting phosphoric acid with sodium hydroxide.

Embodiment 165. The solution of embodiment 156, wherein the phosphate salts are monobasic sodium phosphate and dibasic sodium phosphate.

Embodiment 166. The solution of embodiment 165, wherein the solution has a pH of about pH 5 to about pH 6.

Embodiment 167. The solution of embodiment 166, wherein the solution has a pH of about pH 5.4 to about pH 5.6.

Embodiment 168. The solution of embodiment 166, wherein the solution has a pH of greater than pH 5.4 to about pH 5.6.

Embodiment 169. The solution of embodiment 164, wherein the solution has a pH of about pH 6.5 to about pH 7.5 or a pH of about pH 6.2 to pH 6.8.

Embodiment 166. The solution of embodiment 156, wherein the solution contains less than 100 µg/L of aluminum after storage for at least 12 months (e.g., 12, 13, 14, 15, 16, 17, 18 months or longer) at 25° C. and 40% relative humidity in a sealed container.

Embodiment 167. The solution of any one of embodiments 146 to 166, wherein the solution has an osmolar concentration of about 7 mOsmol/mL to about 7.5 mOsmol/mL, or about 7.4 mOsmol/mL.

Embodiment 168. A sealed container comprising a solution for parenteral administration, wherein the solution is a solution of any one embodiments 146 to 167.

EXAMPLES

The following examples illustrate various iterations of the invention.

Example 1

Sodium Phosphates Injection, USP, 3 mM P/mL (3 millimoles phosphates/mL), is a sterile, nonpyrogenic, concentrated solution containing a mixture of monobasic sodium phosphate and dibasic sodium phosphate in water for injection. Each mL contains 276 mg of monobasic sodium phosphate, monohydrate and 142 mg of dibasic sodium phosphate, anhydrous. The Sodium Phosphates Injection USP monograph specification requires these drug substances to be within a range of 95.0% to 105.0% of label claim, the pH to be 5.0-6.0, and the aluminum content to be no more than (NMT) 180 µg/L (i.e., 180 ppb). The drug product contains no bacteriostat, antimicrobial agent or added buffer.

Attempts to improve the quality of the drug product initially focused on the drug substances, namely monobasic sodium phosphate, monohydrate and dibasic sodium phosphate, as the traditional method for preparing Sodium Phosphates Injection, USP is to prepare an admixture of sodium phosphate monobasic and sodium phosphate dibasic salts in a 2:1 molar ratio (i.e., mix 276 mg/mL of monobasic sodium phosphate, monohydrate and 142 mg/mL of dibasic sodium phosphate, anhydrous in Water for Injection). The drug substances were obtained from multiple vendors and assayed for impurities. Lot-to-lot variability of aluminum, both from a single vendor and among vendors, was higher than desired. The variability and high aluminum content is likely due to the fact that phosphate salts are mined from a quarry, rather than synthesized in a manufacturing plant. Because aluminum is the earth's third most abundant mineral, the phosphate salts are contaminated with aluminum in significant amounts. In addition, the availability of material was low due to limited manufacturing time for high purity material. Based on the high risk of the aluminum content and the vendors' limited manufacturing time and capabilities to support the supply chain, a reliable source for the drug substances could not be secured. Further purification of the drug substances, or the finished drug product, to reduce aluminum was considered but not pursued due to high costs. In situ generation of the drug substances was ultimately pursued as a means to obtain a finished drug product with reproducibly low aluminum content.

The drug substances were generated in situ via two starting materials, phosphoric acid ($H_3PO_4$) and sodium hydroxide (NaOH), by the following reaction: $3H_3PO_4 + 4NaOH \rightarrow Na_2HPO_4 + 2NaH_2PO_4 + 4H_2O$. In solution, the various sodium phosphate species exist in equilibrium. To evaluate the effect of pH on the molar ratios of monobasic sodium phosphate and dibasic sodium phosphate formed in-situ, three 100 mL batches (3 mM P/mL) were prepared with phosphoric acid and titrated with concentrated 10 N sodium hydroxide. Briefly, ortho-phosphoric acid (85%) was added to deionized water cooled on ice; after complete dissolution, 10 N sodium hydroxide was added to adjust the pH to 5.0, 5.5 and 6.0, and the solution was Q.S. to 100 mL with deionized water. Monobasic sodium phosphate monohydrate, sodium phosphate dibasic, and total phosphorus were then assayed by USP compendia methods and the summation of total phosphorus. The results (Table 1) show that a pH of 5.5 achieves the desired label claim of monobasic sodium phosphate monohydrate and dibasic sodium phosphate. In contrast, at a pH of 5.0 and 6.0 the concentrations of monobasic sodium phosphate monohydrate and dibasic sodium phosphates were not within the Sodium Phosphates Injection USP monograph specification range of 95.0% to 105.0% of label claim.

TABLE 1

| | $NaH_2PO_4 \cdot H_2O$ % of Label Claim | $Na_2HPO_4$ % of Label Claim | Total phosphorus/mL |
|---|---|---|---|
| $3H_3PO_4$ + NaOH to pH 5.0 | 58.0% | 119.8% | 2.98 mM |
| $3H_3PO_4$ + NaOH to pH 5.5 | 98.9% | 100.9% | 3.01 mM |
| $3H_3PO_4$ + NaOH to pH 6.0 | 142.5% | 75.9% | 2.94 mM |

Four additional in situ lab batches were prepared as generally described above, except the pH was adjusted to 5.2, 5.4, 5.6 and 5.8, which is slightly tighter than the pH range for the Sodium Phosphates Injection USP monograph range. The results (Table 2) show that at pH of 5.6 both phosphate salts were within the Sodium Phosphates Injection, USP monograph specification range of 95.0% to 105.0% of label claim. In contrast, at a pH of 5.2, 5.4 and 5.8, the concentrations of monobasic sodium phosphate monohydrate and dibasic sodium phosphates were not within the Sodium Phosphates Injection USP monograph specification range of 95.0% to 105.0% of label claim. This experiment demonstrated that the pH range of an in situ formulation must be very close to 5.5 to 5.6 to remain within the Sodium Phosphates Injection, USP monograph specification range of 95.0% to 105.0% of label claim for each phosphate, in order to have the correct ratio of monobasic and dibasic phosphate. Although all 4 batches were low for total phosphorus, the study supports the need to control a tighter pH range than required by the current Sodium Phosphates Injection, USP monograph.

TABLE 2

| | $NaH_2PO_4 \cdot H_2O$ % of Label Claim | $Na_2HPO_4$ % of Label Claim | Total phosphorus/mL |
|---|---|---|---|
| $3H_3PO_4$ + NaOH to pH 5.20 | 66.6% | 110.7% | 2.88 mM |
| $3H_3PO_4$ + NaOH to pH 5.40 | 81.9% | 104.1% | 2.90 mM |
| $3H_3PO_4$ + NaOH to pH 5.60 | 97.1% | 95.8% | 2.89 mM |
| $3H_3PO_4$ + NaOH to pH 5.80 | 114.7% | 86.2% | 2.87 mM |

Example 2

A 10 L batch of Sodium Phosphates Injection, 3 mM P/mL (millimoles/mL) was prepared to evaluate the scale-up process. The batch was made in a 20 L carboy. The quantity of ortho-phosphoric acid (85%) was calculated to total 3 mM phosphates/mL for a 10 Liter solution and added. A 10 N sodium hydroxide solution was slowly added to adjust the pH to 5.5 and the solution was Q.S. to 10 L with deionized water. Monitored solution temperature showed an increase during additions. Cooling was maintained with an ice bath. The bulk solution was filtered using 0.45 um PVDF filter and no change in pH was observed. The results, summarized in Table 3, were within specifications but the exact ratio of monobasic phosphate and dibasic phosphate was not 2 to 1 as per-label claim.

TABLE 3

| | pH | $Na_H2PO_4 \cdot H_2O$ % of Label Claim | $Na_2HPO_4$ % of Label Claim | Total phosphorus/mL |
|---|---|---|---|---|
| $3H_3PO_4$ + NaOH | 5.55 | 95.2% | 105.6% | 2.96 mM |

A second, 10 L (3 mM P/mL) scale-up batch was prepared in a 10 L carboy. For this batch, calculations for the required starting amounts of o-phosphoric acid (85%) and sodium hydroxide were based on stoichiometry concentration of 3 mmol P/mL and 4 mEq Na+/mL, respectively. NaOH pellets were added in small increments with continuous stirring. The solution was allowed to cool between additions utilizing an ice bath, and no addition of NaOH was made with the solution temperature above 40° C. Once all the NaOH was added, the solution was Q.S. to volume and mixed for an additional 10 minutes. The bulk solution was filtered using 0.45 um PVDF filter and no change in pH was observed. The results, shown in Table 4, show the monobasic and dibasic phosphates forms were at about label claim and the total phosphorus were about 3 mM/mL.

TABLE 4

| | pH | $NaH_2PO_4 \cdot H_2O$ % of Label Claim | $Na_2HPO_4$ % of Label Claim | Total phosphorus/mL |
|---|---|---|---|---|
| $3H_3PO_4$ + 4NaOH | 5.55 | 99.2% | 100.6% | 2.99 mM |

Example 3

Three 50 L batches of Sodium Phosphates Injection (3 millimoles P per mL and 4 mEq Na+ per mL) were manufactured, packaged, terminally sterilized and then stored under accelerated (40° C./25% RH) and long term (25° C./40% RH) conditions up to 24 months governed by ICH guidelines. Manufacture of the bulk solution occurred with continuous mixing and temperature control. Water for Injection (WFI) was added to a 100 L mixing bag and cooled to a temperature of about 5-15° C. Ortho-phosphoric acid (85%) was added, and the solution was mixed to achieve complete dissolution. Sodium Hydroxide, NF was slowly added in additions of approx. 1000 g, and pellets were allowed to mix for up to 20 minutes before the next addition. Additions were not made if the temperature of the solution was above 45° C. and, after total addition was complete, the solution was cooled to a temperature of no more than 30° C. Following Q.S. with WFI and final mixing, the bulk solution was obtained. The bulk solution was then filter sterilized (0.2 μm hydrophilic filter) and the sterile filtered bulk solution was filled into a 20 mL cyclic olefin copolymer (COC) plastic vial. Filled vials were then capped, oversealed, and terminally sterilized. Terminal sterilization was shown to not affect drug product phosphates assay values, pH, or phosphate ratio.

Sealed vials were placed on stability and then tested for product stability, or tested on the date placed for stability. Product stability tests included (1) Solution Description, (2) Visual Particulate Matter, (3) pH, (4), total phosphorus, (summation of mono and dibasic phosphate assay results) (5) sodium phosphate monobasic assay (USP Titration), (6) sodium phosphate dibasic assay (USP Titration), (7) particulate matter per container (compliant with USP <788>, Method I USP <1788> light obscuration particle count test), (8) container closure integrity (USP <1207> Dye Ingress Method), and (9) sterility (USP <71> sterility test method). The packaged solution was clear and colorless (Solution Description Test result) and essentially free of visible particulate matter (Visual Particulate Matter Test result) at every time point evaluated. Additional stability attributes are summarized in Table 5 and Table 6.

TABLE 5

| Sample Storage | Test | Date placed | 6M (U) | 6M (I) | 12M (U) | 12M (I) | 18M (I) |
|---|---|---|---|---|---|---|---|
| 1 Long Term | pH | 5.5 | 5.5 | 5.5 | 5.5 | 5.6 | 5.6 |
| | Al Content | 16 μg/L | 11 μg/L | 13 μg/L | 10 μg/L | 9 μg/L | 31 μg/L* |
| | Part. ≥ 10 μm | 204 | 54 | 145 | 21 | 66 | 111 |
| | Part. ≥ 25 μm | 29 | 6 | 8 | 3 | 13 | 38 |
| 1 Accel | pH | 5.5 | 5.5 | 5.5 | NT | NT | NT |
| | Al Content | 16 μg/L | 10 μg/L | 13 μg/L | NT | NT | NT |
| | Part. ≥ 10 μm | 204 | 43 | 38 | NT | NT | NT |
| | Part. ≥ 25 μm | 29 | 6 | 5 | NT | NT | NT |
| 2 Long Term | pH | 5.5 | 5.5 | 5.5 | 5.6 | 5.6 | 5.6 |
| | Al Content | 8 μg/L | 5 μg/L | 10 μg/L | 4 μg/L | 4 μg/L | 29 μg/L* |
| | Part. ≥ 10 μm | 116 | 46 | 82 | 29 | 718 | 274 |
| | Part. ≥ 25 μm | 21 | 4 | 6 | 3 | 137 | 120 |
| 2 Accel | pH | 5.5 | 5.5 | 5.5 | NT | NT | NT |
| | Al Content | 8 μg/L | 2 μg/L | 16 μg/L | NT | NT | NT |
| | Part. ≥ 10 μm | 116 | 61 | 72 | NT | NT | NT |
| | Part. ≥ 25 μm | 21 | 10 | 7 | NT | NT | NT |
| 3 Long Term | pH | 5.5 | 5.5 | 5.5 | 5.6 | 5.6 | 5.6 |
| | Al Content | 12 μg/L | 4 μg/L | 19 μg/L | 6 μg/L | 7 μg/L | 27 μg/L* |
| | Part. ≥ 10 μm | 50 | 76 | 115 | 168 | 122 | 37 |
| | Part. ≥ 25 μm | 9 | 3 | 10 | 56 | 39 | 10 |

TABLE 5-continued

| Sample Storage | Test | Date placed | 6M (U) | 6M (I) | 12M (U) | 12M (I) | 18M (I) |
|---|---|---|---|---|---|---|---|
| 3 | pH | 5.5 | 5.5 | 5.5 | NT | NT | NT |
| Accel | Al Content | 12 µg/L | 14 µg/L | 14 µg/L | NT | NT | NT |
|  | Part. ≥ 10 µm | 50 | 64 | 83 | NT | NT | NT |
|  | Part. ≥ 25 µm | 9 | 5 | 11 | NT | NT | NT |

Test 1 - Sodium Phosphate Monobasic, Assay
Test 2 - Sodium Phosphate Dibasic, Assay
Test 3 - Total Phosphorous
Accel - 40° C./25% relative humidity (RH); Long Term - 25° C./40% RH
*Tested at 22 months
NT—Not Tested; M—Month; I—Inverted; U—Upright; Al—Aluminum; Part.—particulate

TABLE 6

| Sample Storage | Test | Date placed | 6M (U) | 6M (I) | 12M (U) | 12M (I) | 18M (I) |
|---|---|---|---|---|---|---|---|
| 1 | 1 | 100.1% | 101.4% | 101.9% | 100.6% | 100.0% | 101.2% |
| Long | 2 | 99.1% | 99.6% | 100.3% | 99.4% | 100.0% | 99.5% |
| Term | 3 | 99.8% | 100.8% | 101.4% | 100.2% | 100.2% | 100.7% |
| 1 | 1 | 100.1% | 101.7% | 97.4% | NT | NT | NT |
| Accel | 2 | 99.1% | 100.0% | 95.7% | NT | NT | NT |
|  | 3 | 99.8% | 101.1% | 96.8% | NT | NT | NT |
| 2 | 1 | 98.3% | 97.2% | 99.9% | 97.2% | 97.5% | 98.6% |
| Long | 2 | 101.3% | 102.3% | 102.5% | 101.6% | 101.8% | 103.2% |
| Term | 3 | 99.3% | 98.9% | 100.7% | 98.7% | 98.9% | 100.1% |
| 2 | 1 | 98.3% | 99.1% | 100.0% | NT | NT | NT |
| Accel | 2 | 101.3% | 101.7% | 102.6% | NT | NT | NT |
|  | 3 | 99.3% | 100.0% | 100.9% | NT | NT | NT |
| 3 | 1 | 100.1% | 101.0% | 99.3% | 98.4% | 99.7% | 100.1% |
| Long | 2 | 100.1% | 100.2% | 99.7% | 99.2% | 99.7% | 99.3% |
| Term | 3 | 100.1% | 100.7% | 99.4% | 98.6% | 99.7% | 99.9% |
| 3 | 1 | 100.1% | 102.1% | 101.8% | NT | NT | NT |
| Accel | 2 | 100.1% | 101.1% | 101.2% | NT | NT | NT |
|  | 3 | 100.1% | 101.8% | 101.% | NT | NT | NT |

Test 1 - Sodium Phosphate Monobasic, Assay
Test 2 - Sodium Phosphate Dibasic, Assay
Test 3 - Total Phosphorus
Accel - 40° C./25% relative humidity (RH); Long Term - 25° C./40% RH
NT—Not Tested; M—Month; I—Inverted; U—Upright Example 4

Potassium Phosphates Injection, USP, 3 mM P/mL (3 millimoles total phosphorus per milliliter), is a sterile, nonpyrogenic, concentrated solution containing a mixture of monobasic potassium phosphate and dibasic potassium phosphate in Water for Injection. Each mL contains 224 mg of monobasic potassium phosphate (anhydrous) and 236 mg of dibasic potassium phosphate (anhydrous). The Potassium Phosphates Injection USP monograph requires these drug substances to be within a range of 95.0% to 105.0% of label claim, the pH to be 6.5-7.5, and the aluminum content to be no more than (NMT) 15,000 µg/L (i.e., 15,000 ppb). The drug product contains no bacteriostat, antimicrobial agent or added buffer.

As per the USP method, a 3 mM P/mL and 4.4 mEq K+/mL potassium phosphates solution was prepared by dissolving 22.4 g of potassium phosphate monobasic and 23.6 g of potassium phosphate dibasic in Water for Injection and adjusting the final volume of the solution to 100 mL. The pH values obtained for the product prepared as per USP ranged from 6.43 to 6.48. Attempts to improve the quality of the drug product initially focused on the drug substances, namely monobasic potassium phosphate, monohydrate and dibasic potassium phosphate. The drug substances were obtained from multiple vendors and assayed for impurities. Lot-to-lot variability of aluminum, both from a single vendor and among vendors, was higher than desired. In addition, the availability of material was low due to limited manufacturing time. Based on the high risk of the aluminum content and the vendors' limited manufacturing time and capabilities to support the supply chain, a reliable source for the drug substances could not be secured. Further purification of the drug substances, or the finished drug product, to reduce aluminum was considered but not pursued due to high costs. In situ generation of the drug substances was ultimately pursued as a means to obtain a finished drug product with reproducibly low aluminum content.

The drug substances were generated in situ via two starting materials, phosphoric acid ($H_3PO_4$) and potassium hydroxide (KOH), by the following reaction: $3H_3PO_4 + 4KOH \rightarrow K_2HPO_4 + 2KH_2PO_4 + 4H_2O$. In solution, the various potassium phosphate species exist in equilibrium. Upon addition of phosphoric acid to potassium hydroxide, monobasic and dibasic potassium phosphates are formed in solution. The pKa values of the triprotic phosphoric acid when titrated with potassium hydroxide were experimentally determined to be pH 1.7 ($pKa_1$), pH 6.6 ($pKa_2$), and pH 11.4 ($pKa_3$). The fraction of potassium phosphate species existing as monobasic or dibasic potassium phosphate is dependent on the pH of the solution. Using the experimentally determined pKa values and a total concentration of 3 molar phosphate, the fraction of monobasic and dibasic potassium phosphate at select pH values were predicted (Table 7).

TABLE 7

Predicted Amounts of Monobasic and Dibasic Potassium Phosphate at Select pH Values (fractions are mol %)

| pH | Fraction monobasic ($KH_2PO_4$) | Fraction dibasic ($K_2HPO_4$) | Concentration monobasic ($KH_2PO_4$) | Concentration dibasic ($K_2HPO_4$) | Total Phosphorus concentration | Potassium Concentration (mEq/mL) |
|---|---|---|---|---|---|---|
| 6.40 | 0.613 | 0.387 | 1.84 molar | 1.16 molar | 3.00 molar | 4.16 |
| 6.41 | 0.608 | 0.392 | 1.82 molar | 1.18 molar | 3.00 molar | 4.18 |
| 6.42 | 0.602 | 0.398 | 1.81 molar | 1.19 molar | 3.00 molar | 1.19 |
| 6.43 | 0.597 | 0.403 | 1.79 molar | 1.21 molar | 3.00 molar | 4.21 |
| 6.44 | 0.591 | 0.409 | 1.77 molar | 1.23 molar | 3.00 molar | 4.23 |
| 6.45 | 0.585 | 0.414 | 1.76 molar | 1.24 molar | 3.00 molar | 4.24 |
| 6.46 | 0.580 | 0.420 | 1.74 molar | 1.26 molar | 3.00 molar | 4.26 |
| 6.47 | 0.574 | 0.426 | 1.72 molar | 1.28 molar | 3.00 molar | 4.28 |
| 6.48 | 0.569 | 0.431 | 1.71 molar | 1.29 molar | 3.00 molar | 4.29 |
| 6.49 | 0.563 | 0.437 | 1.69 molar | 1.31 molar | 3.00 molar | 4.31 |
| 6.50 | 0.557 | 0.443 | 1.67 molar | 1.33 molar | 3.00 molar | 4.33 |
| 6.51 | 0.551 | 0.448 | 1.65 molar | 1.35 molar | 3.00 molar | 4.35 |
| 6.52 | 0.546 | 0.454 | 1.64 molar | 1.36 molar | 3.00 molar | 4.36 |
| 6.53 | 0.540 | 0.460 | 1.62 molar | 1.38 molar | 3.00 molar | 4.38 |
| 6.54 | 0.534 | 0.466 | 1.60 molar | 1.40 molar | 3.00 molar | 4.40 |
| 6.55 | 0.529 | 0.471 | 1.59 molar | 1.41 molar | 3.00 molar | 4.41 |
| 6.56 | 0.523 | 0.477 | 1.57 molar | 1.43 molar | 3.00 molar | 4.43 |
| 6.57 | 0.517 | 0.483 | 1.55 molar | 1.45 molar | 3.00 molar | 4.45 |
| 6.58 | 0.512 | 0.488 | 1.53 molar | 1.47 molar | 3.00 molar | 4.47 |
| 6.59 | 0.506 | 0.494 | 1.52 molar | 1.48 molar | 3.00 molar | 4.48 |
| 6.60 | 0.500 | 0.500 | 1.50 molar | 1.50 molar | 3.00 molar | 4.50 |

Potassium Phosphates Injection, USP, 3 mM P/mL is labeled to contain 1.65 M monobasic potassium phosphate and 1.35 molar dibasic potassium phosphate, and the concentration of the monobasic and dibasic potassium phosphates should be within 95% to 105% of these target concentrations (per USP requirements). Given the data in Table 7, the acceptable pH range for the drug product—i.e., the pH range that will satisfy USP requirements for total phosphorus—was theoretically determined to be 6.48-6.55. Within this pH range, potassium is also within 95%-105% of the labeled amount (i.e., 4.4 mEq/mL).

The feasibility of producing Potassium Phosphates Injection, USP through reaction of o-Phosphoric acid and Potassium hydroxide in situ was also assessed experimentally. Briefly, potassium hydroxide, sufficient to provide a 4.4 mEq/mL K+ concentration (24.69 g; weight not adjusted for assay), was dissolved in 60 mL of deionized water. o-Phosphoric acid, sufficient to provide a 3 molar concentration (29.4 g; weight not adjusted for assay) was added slowly to the potassium hydroxide solution. Since, the reaction is exothermic, the solution was then cooled to room temperature and the volume was adjusted to 100 mL with deionized water. The final pH of the solution was pH 6.57.

The amount of monobasic and dibasic potassium phosphates were determined by titration with sodium hydroxide and hydrochloric acid as per USP methods. The results are summarized in Table 8. Potassium phosphate solution prepared in this manner yielded amounts of monobasic and dibasic potassium phosphates within the USP specified range of 95% to 105% when compared to reference (Fresenius Kabi USA, LLC). The amount of potassium ions is equivalent to the amount of potassium hydroxide added. As 440 mmol of potassium hydroxide was added for 100 mL of solution, this results in a concentration of 4.4 mEq potassium/mL.

TABLE 8

Amount Monobasic and Dibasic Potassium Phosphate in Experimentally Prepared Solution

| Species | Amount in 100 mL | Reference | % Reference |
|---|---|---|---|
| Monobasic ($KH_2PO_4$) | 21.57 g (1.59 molar) | 22.4 g (1.65 molar) | 96.28% |
| Dibasic ($K_2HPO_4$) | 24.25 g (1.39 molar) | 23.6 g (1.35 molar) | 102.77% |

Example 5

Three batches of Potassium Phosphates Injection (3 millimoles P per mL and 4.7 mEq K+ per mL) were manufactured, packaged, terminally sterilized and then stored under accelerated (40° C./25% RH) and long term (25° C./40% RH) conditions up to 24 months governed by ICH guidelines. Manufacturing was as generally described in Example 3, except the order of addition for the o-phosphoric acid and cationic base were reversed.

Sealed vials were placed on stability and then tested for product stability, or tested on the date placed for stability. Product stability tests included (1) Solution Description, (2) Visual Particulate Matter, (3) pH, (4), total phosphorus, (summation of mono and dibasic phosphate assay results) (5) potassium phosphate monobasic assay (USP Titration), (6) potassium phosphate dibasic assay (USP Titration), (7) particulate matter per container (compliant with USP <788>, Method I USP <1788> light obscuration particle count test), (8) container closure integrity (USP <1207> Dye Ingress Method), and (9) sterility (USP <71> sterility test method). The packaged solution was clear and colorless (Solution Description Test result) and essentially free of visible particulate matter (Visual Particulate Matter Test result) at every time point evaluated. Additional stability attributes are summarized in Table 9 and Table 10.

TABLE 9

| Sample - Storage | Test | Date placed | 3M (I) | 6M (U) | 6M (I) |
|---|---|---|---|---|---|
| 1 - Long Term | pH | 6.7 | 6.5 | 6.5 | 6.5 |
| | Al Content | 0 µg/L | 0 µg/L | NT | NT |
| | Part. ≥10 µm | 361 | 29 | 214 | 64 |
| | Part. ≥25 µm | 134 | 1 | 74 | 7 |
| 1 - Accel | pH | 6.7 | 6.5 | 6.5 | 6.5 |
| | Al Content | 0 µg/L | 0 µg/L | NT | 14 µg/L |
| | Part. ≥10 µm | 361 | 18 | 62 | 33 |
| | Part. ≥25 µm | 134 | 3 | 13 | 5 |
| 2 - Long Term | pH | 6.7 | 6.5 | 6.5 | 6.5 |
| | Al Content | 35 µg/L | 0 µg/L | NT | NT |
| | Part. ≥10 µm | 7 | 17 | 195 | 115 |
| | Part. ≥25 µm | 0 | 4 | 63 | 37 |
| 2 - Accel | pH | 6.7 | 6.5 | 6.5 | 6.5 |
| | Al Content | 35 µg/L | 0 µg/L | NT | 57 µg/L |
| | Part. ≥10 µm | 7 | 19 | 63 | 84 |
| | Part. ≥25 µm | 0 | 2 | 19 | 18 |
| 3 - Long Term | pH | 6.7 | 6.5 | 6.5 | 6.5 |
| | Al Content | 77 µg/L | 0 µg/L | NT | NT |
| | Part. ≥10 µm | 146 | 7 | 64 | 64 |
| | Part. ≥25 µm | 39 | 2 | 14 | 4 |
| 3 - Accel | pH | 6.7 | 6.5 | 6.5 | 6.5 |
| | Al Content | 77 µg/L | 0 µg/L | NT | 73 µg/L |
| | Part. ≥10 µm | 146 | 13 | 41 | 94 |
| | Part. ≥25 µm | 39 | 0 | 9 | 19 |
| 4 - Long Term | pH | 6.5 | 6.5 | 6.5 | 6.5 |
| | Al Content | 37 µg/L | 87 µg/L | NT | 5 µg/L |
| | Part. ≥10 µm | 229 | 156 | 697 | 458 |
| | Part. ≥25 µm | 24 | 20 | 100 | 50 |
| 4 - Accel | pH | 6.5 | 6.5 | 6.6 | 6.6 |
| | Al Content | 37 µg/L | 67 µg/L | NT | 13 µg/L |
| | Part. ≥10 µm | 229 | 127 | 69 | 223 |
| | Part. ≥25 µm | 24 | 16 | 10 | 26 |
| 5 - Long Term | pH | 6.6 | 6.5 | 6.6 | 6.6 |
| | Al Content | 59 µg/L | 57 µg/L | NT | 26 µg/L |
| | Part. ≥10 µm | 60 | 453 | 590 | 148 |
| | Part. ≥25 µm | 18 | 33 | 81 | 12 |
| 5 - Accel | pH | 6.6 | 6.5 | 6.6 | 6.6 |
| | Al Content | 59 µg/L | 53 µg/L | NT | 10 µg/L |
| | Part. ≥10 µm | 60 | 156 | 196 | 161 |
| | Part. ≥25 µm | 18 | 29 | 22 | 27 |
| 6 - Accel. | pH | 6.6 | 6.5 | 6.6 | 6.6 |
| | Al Content | 28 µg/L | 85 µg/L | NT | 30 µg/L |
| | Part. ≥10 µm | 92 | 181 | 92 | 92 |
| | Part. ≥25 µm | 9 | 18 | 16 | 10 |
| 6 - Accel | pH | 6.6 | 6.5 | 6.6 | 6.6 |
| | Al Content | 28 µg/L | 35 µg/L | NT | 9 µg/L |
| | Part. ≥10 µm | 92 | 252 | 457 | 326 |
| | Part. ≥25 µm | 9 | 41 | 106 | 72 |

Accel - 40° C./25% relative humidity (RH);
Long Term - 25° C./40% RH
NT—Not Tested;
M—Month;
I—Inverted;
U—Upright;
Al—Aluminum;
Part.—particulate

TABLE 10

| Sample Storage | Test | Date placed | 3M (I) | 6M (U) | 6M (I) |
|---|---|---|---|---|---|
| 1 Long Term | 1 | 97.7% | 98.4% | 96.4% | 95.8% |
| | 2 | 101.3% | 101.4% | 100.4% | 100.7% |
| | 3 | 99.4% | 98.9% | 98.2% | 98.0% |
| 1 Accel | 1 | 97.7% | 98.5% | 96.2% | 96.3% |
| | 2 | 101.3% | 101.9% | 100.6% | 100.8% |
| | 3 | 99.4% | 100.0% | 98.2% | 98.4% |
| 2 Long Term | 1 | 98.6% | 99.3% | 97.0% | 97.2% |
| | 2 | 100.8% | 100.9% | 99.9% | 100.1% |
| | 3 | 99.6% | 100.1% | 98.4% | 98.5% |
| 2 Accel | 1 | 98.6% | 99.8% | 97.8% | 97.5% |
| | 2 | 100.8% | 101.5% | 100.2% | 100.2% |
| | 3 | 99.6% | 100.5% | 98.9% | 98.7% |
| 3 Long Term | 1 | 99.1% | 100.6% | 98.6% | 98.4% |
| | 2 | 97.3% | 98.7% | 97.9% | 98.1% |
| | 3 | 98.3% | 99.8% | 98.3% | 98.3% |
| 3 Accel | 1 | 99.1% | 101.0% | 98.3% | 98.9% |
| | 2 | 97.3% | 99.2% | 97.6% | 98.0% |
| | 3 | 98.3% | 100.2% | 98.0% | 98.5% |
| 4 Long Term | 1 | 101.7% | 102.4% | 102.1% | 101.8% |
| | 2 | 101.2% | 102.0% | 101.3% | 101.8% |
| | 3 | 101.5% | 102.2% | 101.8% | 101.8% |
| 4 Accel | 1 | 101.7% | 100.1% | 101.9% | 101.7% |
| | 2 | 101.2% | 99.8% | 102.0% | 101.8% |
| | 3 | 101.5% | 100.0% | 101.9% | 101.8% |
| 5 Long Term | 1 | 100.8% | 100.8% | 99.7% | 99.9% |
| | 2 | 100.2% | 100.3% | 99.7% | 99.7% |
| | 3 | 100.5% | 100.6% | 99.7% | 99.8% |
| 5 Accel | 1 | 100.8% | 100.8% | 100.0% | 100.1% |
| | 2 | 100.2% | 100.3% | 100.4% | 100.1% |
| | 3 | 100.5% | 100.6% | 100.2% | 100.1% |
| 6 Long Term | 1 | 100.5% | 100.9% | 99.8% | 99.8% |
| | 2 | 100.1% | 100.6% | 100.8% | 100.7% |
| | 3 | 100.3% | 100.8% | 100.3% | 100.2% |
| 6 Accel | 1 | 100.5% | 101.2% | 100.4% | 100.4% |
| | 2 | 100.1% | 101.3% | 101.4% | 100.9% |
| | 3 | 100.3% | 101.3% | 100.9% | 100.6% |

Test 1 - Sodium Phosphate Monobasic, Assay
Test 2 - Sodium Phosphate Dibasic, Assay
Test 3 - Total Phosphorus
Accel - 40° C./25% relative humidity (RH);
Long Term - 25° C./40% RH
NT—Not Tested;
M—Month;
I—Inverted;
U—Upright The three batches of Sodium Phosphates Injection described in Example 3 were analyzed for potential leachable compounds (e.g., volatile, semi-volatile, non-volatile, elemental) from manufacturing components through to the container closure system. The evaluation of leachables showed that the drug product is safe with respect to leachables content and there is no noticeable trend in leachable amounts with temperature.

In particular, elemental leachables were evaluated using inductively coupled plasma mass spectrometry. The results for the elemental leachables analysis is summarized in Table 11. These results show that even after storage of inverted vials for 6 months at 25° C. and 40% relative humidity (25/40) or 40° C. and 25% relative humidity (40/25), elemental impurities are extremely low.

TABLE 11

Elemental Impurity Leachables Results for Sodium Phosphates Injection

| Element | QL (ppb) | Parenteral PDE (µg/day) | AEC (ppb) | 1 25/40 (ppb) | 1 40/25 (ppb) | 2 25/40 (ppb) | 2 40/25 (ppb) | 3 25/40 (ppb) | 3 40/25 (ppb) |
|---|---|---|---|---|---|---|---|---|---|
| Iron | 0.17 | 3500 | 1064113 | 115.19 | 105.54 | 115.10 | 129.50 | 99.87 | 102.34 |
| Molybdenum | 0.01 | 1500 | 456048 | 7.43 | 7.56 | 6.70 | 5.98 | 5.07 | 5.10 |
| Zinc | 0.29 | 1500 | 456048 | 205.61 | 189.27 | 210.62 | 90.03 | 77.63 | 78.39 |
| Chromium | 0.04 | 1100 | 334435 | 14.56 | 15.14 | 15.81 | 15.02 | 15.66 | 15.06 |
| Barium | 0.03 | 700 | 212823 | 4.75 | 3.41 | 3.22 | 2.44 | 3.31 | 4.14 |
| Manganese | 0.02 | 700 | 212823 | 2.63 | 3.05 | 3.03 | 3.30 | 2.44 | 2.23 |
| Tin | 0.01 | 600 | 182419 | ND | ND | ND | ND | ND | ND |
| Copper | 0.04 | 300 | 91210 | 4.98 | 3.68 | 5.84 | 24.70 | 0.76 | 0.27 |
| Lithium | 0.005 | 250 | 76008 | <QL | ND | ND | ND | ND | ND |
| Gold | 0.07 | 100 | 30403 | <QL | <QL | ND | 0.07 | <QL | 0.10 |
| Antimony | 0.02 | 90 | 27363 | 112.01 | 111.19 | 117.23 | 118.71 | 121.70 | 118.82 |
| Selenium | 0.27 | 80 | 24323 | 1.95 | <QL | 2.08 | 2.11 | 4.47 | 4.61 |
| Nickel | 0.02 | 20 | 6081 | 219.42 | 211.58 | 242.78 | 237.47 | 235.78 | 239.74 |
| Arsenic | 0.03 | 15 | 4560 | 1.05 | 0.80 | 0.15 | 1.37 | 0.25 | 0.67 |
| Vanadium | 0.08 | 10 | 3040 | ND | ND | ND | ND | ND | ND |
| Silver | 0.01 | 10 | 3040 | ND | ND | ND | ND | ND | ND |
| Ruthenium | 0.001 | 10 | 3040 | ND | 0.03 | ND | ND | ND | ND |
| Rhodium | 0.003 | 10 | 3040 | 0.06 | 0.05 | 0.03 | 0.04 | 0.02 | 0.03 |
| Platinum | 0.007 | 10 | 3040 | ND | ND | ND | ND | ND | ND |
| Palladium | 0.02 | 10 | 3040 | 0.02 | 0.02 | 0.03 | ND | 0.01 | 0.02 |
| Osmium | 0.008 | 10 | 3040 | 0.24 | 0.31 | 0.29 | 0.24 | 0.29 | 0.24 |
| Iridium | 0.001 | 10 | 3040 | 0.08 | 0.08 | 0.07 | 0.04 | 0.03 | 0.04 |
| Thallium | 0.004 | 8 | 2432 | <QL | <QL | 0.005 | <QL | 0.005 | <QL |
| Cobalt | 0.09 | 5 | 1520 | 0.60 | 0.41 | 0.40 | 0.32 | 0.21 | 0.64 |
| Lead | 0.004 | 5 | 1520 | 0.19 | 0.31 | 2.21 | 5.47 | 0.30 | 0.24 |
| Mercury | 0.01 | 3 | 912 | 1.26 | 0.87 | 0.59 | 0.25 | 0.51 | 0.42 |
| Cadmium | 0.002 | 2 | 608 | 0.05 | 0.05 | 0.05 | 0.03 | 0.03 | 0.03 |
| Aluminum | 180 | N/A | 180 | ND | ND | 5.60 | ND | ND | ND |

What is claimed is:

1. A solution for parenteral administration comprising potassium phosphate salts in an amount that provides to the solution about 3 millimoles/mL total phosphorus and a pharmaceutically acceptable carrier in a sealed container, wherein the solution contains less than 250 µg/L of aluminum after storage for 12 months at 25° C. and 40% relative humidity, and wherein the phosphate salts are formed in situ by reacting phosphoric acid with a cationic base.

2. The solution of claim 1, wherein the solution contains less than 200 µg/L of aluminum after storage for 12 months at 25° C. and 40% relative humidity in a sealed container.

3. The solution of claim 2, wherein the solution contains less than 100 µg/L of aluminum after storage for 12 months at 25° C. and 40% relative humidity in a sealed container.

4. The solution of claim 1, wherein the pharmaceutically acceptable carrier is Water for Injection, saline, or a dextrose solution.

5. The solution of claim 1, wherein the phosphate salts are formed in situ by reacting phosphoric acid with potassium hydroxide.

6. The solution of 1, wherein the phosphate salts are monobasic potassium phosphate and dibasic potassium phosphate.

7. The solution of claim 1, wherein the solution has a pH of about pH 6 to about pH 8.

8. The solution of claim 1, wherein the solution has a pH of about pH 6.5 to about pH 7.5 or a pH of about pH 6.2 to pH 6.8.

9. A solution for parenteral administration comprising potassium phosphate salts in a pharmaceutically acceptable carrier, wherein the solution contains less than about 250 µg/L of aluminum and has no more than 0.00309 millimoles of aluminum for every mole of phosphorus provided by the potassium phosphate salts, wherein the phosphate salts are formed in situ by reacting phosphoric acid with a cationic base.

10. The solution of claim 9, wherein the solution contains less than about 250 µg/L of aluminum and has no more than 0.00309 millimoles of aluminum for every mole of phosphorus in the solution.

11. The solution of claim 9, wherein the solution contains less than about 200 µg/L of aluminum.

12. The solution of claim 9, wherein the solution contains less than about 100 µg/L of aluminum.

13. The solution of claim 9, wherein the pharmaceutically acceptable carrier is Water for Injection, saline, or a dextrose solution.

14. The solution of claim 9, wherein the phosphate salts are formed in situ by reacting phosphoric acid with potassium hydroxide.

15. The solution of claim 9, wherein the phosphate salts are monobasic potassium phosphate and dibasic potassium phosphate.

16. The solution of claim 15, wherein the solution has a pH of about pH 6 to about pH 8.

17. The solution of claim 16, wherein the solution has a pH of about pH 6.5 to about pH 7.5 or a pH of about pH 6.2 to pH 6.8.

18. The solution of claim 9, wherein the solution contains less than 250 µg/L of aluminum after storage for 12 months at 25° C. and 40% relative humidity in a sealed container.

* * * * *